(12) United States Patent
Paul

(10) Patent No.: US 9,421,262 B2
(45) Date of Patent: Aug. 23, 2016

(54) COMPOSITIONS AND METHODS FOR TREATING DERMATOLOGICAL CONDITIONS

(75) Inventor: Harbhajan S. Paul, Wexford, PA (US)

(73) Assignee: Biomed Research & Technologies, Inc., Wexford, PA (US)

( * ) Notice: Subject to any disclaimer, the term of this patent is extended or adjusted under 35 U.S.C. 154(b) by 395 days.

(21) Appl. No.: 12/607,470

(22) Filed: Oct. 28, 2009

(65) Prior Publication Data
US 2011/0098229 A1  Apr. 28, 2011

(51) Int. Cl.
| | | |
|---|---|---|
| A61K 31/198 | (2006.01) | |
| A61K 31/6615 | (2006.01) | |
| A61K 38/06 | (2006.01) | |
| A61K 31/7076 | (2006.01) | |
| A61K 31/19 | (2006.01) | |
| A61K 31/194 | (2006.01) | |
| A61K 31/575 | (2006.01) | |
| A61K 31/22 | (2006.01) | |
| A61K 31/23 | (2006.01) | |
| A61K 31/4415 | (2006.01) | |
| A61K 31/4188 | (2006.01) | |
| A61K 31/355 | (2006.01) | |
| A61K 31/51 | (2006.01) | |
| A61K 31/4406 | (2006.01) | |
| A61K 31/375 | (2006.01) | |
| A61K 31/695 | (2006.01) | |
| A61P 17/00 | (2006.01) | |
| A61K 45/06 | (2006.01) | |
| A61K 9/00 | (2006.01) | |
| A61K 9/06 | (2006.01) | |
| A61K 36/185 | (2006.01) | |
| A61K 36/286 | (2006.01) | |
| A61K 36/63 | (2006.01) | |
| A61K 36/889 | (2006.01) | |

(52) U.S. Cl.
CPC .............. *A61K 45/06* (2013.01); *A61K 9/0014* (2013.01); *A61K 9/06* (2013.01); *A61K 31/19* (2013.01); *A61K 31/194* (2013.01); *A61K 31/198* (2013.01); *A61K 31/22* (2013.01); *A61K 31/23* (2013.01); *A61K 31/355* (2013.01); *A61K 31/375* (2013.01); *A61K 31/4188* (2013.01); *A61K 31/4406* (2013.01); *A61K 31/4415* (2013.01); *A61K 31/51* (2013.01); *A61K 31/575* (2013.01); *A61K 31/6615* (2013.01); *A61K 31/695* (2013.01); *A61K 31/7076* (2013.01); *A61K 36/185* (2013.01); *A61K 36/286* (2013.01); *A61K 36/63* (2013.01); *A61K 36/889* (2013.01); *A61K 38/06* (2013.01)

(58) Field of Classification Search
CPC . A61K 2300/00; A61K 31/19; A61K 31/194; A61K 31/198; A61K 31/22; A61K 31/23; A61K 31/355; A61K 31/375; A61K 31/4188; A61K 31/4406; A61K 31/4415; A61K 31/51; A61K 31/575; A61K 31/6615; A61K 31/7076; A61K 36/185; A61K 36/286; A61K 36/63; A61K 36/889; A61K 38/06; A61K 45/06; A61K 9/0014; A61K 9/06
USPC ............................................................ 514/2
See application file for complete search history.

(56) References Cited

U.S. PATENT DOCUMENTS

| | | | |
|---|---|---|---|
| 4,201,235 A | 5/1980 | Ciavatta | |
| 4,456,596 A | 6/1984 | Schaefer | |
| 4,495,079 A | 1/1985 | Good | |
| 4,707,354 A * | 11/1987 | Garlen et al. | 424/47 |
| 4,732,892 A | 3/1988 | Sarpotdar et al. | |
| 4,760,096 A | 7/1988 | Sakai et al. | |
| 4,859,653 A | 8/1989 | Morelle et al. | |
| 4,954,532 A * | 9/1990 | Elliott et al. | 514/63 |
| 5,079,003 A * | 1/1992 | Scaffidi | 424/401 |
| 5,091,171 A | 2/1992 | Yu et al. | |
| 5,175,190 A | 12/1992 | Burton et al. | |
| 5,204,099 A | 4/1993 | Barbier et al. | |
| 5,385,938 A | 1/1995 | Yu et al. | |
| 5,407,958 A * | 4/1995 | Heath et al. | 514/546 |
| 5,425,954 A | 6/1995 | Thompson et al. | |
| 5,470,880 A | 11/1995 | Yu et al. | |
| 5,472,698 A | 12/1995 | Rawlings et al. | |
| 5,520,991 A | 5/1996 | Eustatiu | |
| 5,561,158 A | 10/1996 | Yu et al. | |
| 5,569,461 A | 10/1996 | Andrews | |
| 5,643,899 A | 7/1997 | Elias et al. | |
| 5,658,580 A | 8/1997 | Mausner | |
| 5,681,853 A | 10/1997 | Yu et al. | |
| 5,866,537 A | 2/1999 | Bianchi | |
| 6,149,924 A * | 11/2000 | Paul | 424/401 |
| 6,596,287 B2 * | 7/2003 | Deckers et al. | 424/401 |
| 2008/0167378 A1 * | 7/2008 | Fukatsu | A61K 31/192 514/568 |

FOREIGN PATENT DOCUMENTS

WO  00/04870 A2  2/2000

OTHER PUBLICATIONS

Van Leet et al. ("Effectiveness of the Ascomycin Macrolactam SDZ ASM 981 in the Topical Treatment of Atopic Dermatitis," Arch. Dermatol., 1998, 134, 805-809).*

(Continued)

*Primary Examiner* — James H Alstrum Acevedo
*Assistant Examiner* — Tara Martinez
(74) *Attorney, Agent, or Firm* — Beck & Thomas, P.C.

(57) ABSTRACT

Provided herein are methods of improving one or more symptoms of a dermatological condition in a patient. The methods comprise topically administering a topical composition to the patient comprising a branched chain amino acid, and an enzyme activator. Also provided are kits comprising the topical composition and optionally a topical steroid.

23 Claims, 4 Drawing Sheets

(56) References Cited

OTHER PUBLICATIONS

Aalto-Korte et al. ("Pharmacokinetics of topical hydrocortisone at plasma level after applications once or twice daily in patients with widespread dermatitis." British Journal of Dermatology, 1995, 133, 259-263).*
(Cleveland Clinic—Pruritis—accessed Apr. 28, 2014).*
Mayo Clinic—Dematomysositis Treatment, Jul. 7, 2011.*
Medscape—Leukemia Curtis Treatment and Management, Jul. 10, 2012).*
DermNet NZ—atopic dermatitis, Feb. 2004.*
International Searching Authority, Notification of Transmittal of International Search Report and the Written Opinion of the International Searching Authority, or the Declaration, Apr. 1, 2011.
Harbhajan S. Paul, Assessment of Effect of Starvation, Glucose, Fatty Acids and Hormones on a-Decarboxylation of Leucine in Skeletal Muscle of Rat, Journal of Nutrition, 1976, pp. 1079-1088, vol. 106.
Harbhajan S. Paul, Effect of carnitine on branched-chain amino acid oxidation by liver and skeletal muscle, Journal of Physiology, 1978, pp. E494-E499, vol. 234.
Harbhajan S. Paul, Mechanism of Increased Conversion of Branched Chain Keto Acid Dehydrogenase from Inactive to Active Form by a Medium Chain Fatty Acid (Octanoate) in Skeletal Muscle, Journal of Biological Chemistry, 1992, pp. 11208-11214, vol. 267.
Victor R. Wheatley, Lipogenesis from amino acids in perfused isolated dog skin, Journal of Lipid Research, 1967, pp. 84-89, vol. 8.
Oystein Spydevold, The effect of octanoate and palmitate on the metabolism of valine in perfused hindquater of rat, European Journal of Biochemistry, 1979, pp. 389-394, vol. 97.
Nicolaides, Skin Lipids: Their Biochemical Uniqueness, Science, 1974, pp. 19-26, vol. 186.
Nancy Rodriguez, Trioctanoin infusion increases in vivo leucine oxidation: a lesson in isotope modeling, American Journal of Physiology, 1986, pp. E343-E348, vol. 251.
Hirosuke Oku, Precursor role of branched-chain amino acids in the biosynthesis of iso and anteiso fatty acids in rat skin, Biochimica et Biophysica Acta, 1994, pp. 279-287, vol. 1214.
Instituto Mexicano De La Propiedad Industrial, Examiner's Adverse Report for Mexican Patent Application No. MX/a/2012/005126, Apr. 29, 2013.
Wheatley, Lipkin, Woo: Lipogenesis from amino acids in perfused isolated dog skin. J. Lip. Res. 8: 84-89, 1967.
Nicolaides: Skin Lipids: Their Biochemical Uniqueness. Science 186: 19-26, 1974.
Paul, Adibi: Assessment of effect of starvation, glucose, fatty acids and hormones on •-decarboxylationof leucine in skeletal muscle of rat. J. Nutr. 106: 1079-1088, 1976.
Paul, Adibi: Leucine oxidation in diabetes and starvation; Effect of ketone bodies on branched-chain amino acid oxidation in vitro. Metabolism 27:185-200, 1978.
Paul, Adibi: Effect of carnitine on branched-chain amino acid oxidation by liver and skeletal muscle. Am. J. Physiol. 234: E494-E499, 1978.
Spydevold: The effect of octanoate and palmitate on the metabolism of valine in perfused hindquarter of rat. Eur. J. Biochem. 97: 389-394, 1979.
Paul, Adibi: Leucine oxidation and protein turnover in clofibrate-induced muscle protein degradation in rats. J. Clin. Invest. 65: 1285-1293, 1980.
Paul, Adibi: Role of ATP in the regulation of branched-chain a-keto acid dehydrogenase activity in liver and muscle mitochondria of fed, fasted, and diabetic rats. J, Biol. Chem. 257: 4875-4881, 1982.
Paul, Adibi: Activation of hepatic branched chain a-keto acid dehydrogenase by a skeletal muscle factor. J. Biol. Chem. 257: 12581-12588, 1982.
Paul, Adibi: Regulation of branched chain amino acid catabolism. In: Branched Chain Amino and Keto Acids in Heath and Disease. 182-219, 1983.
Paul, Adibi: A possible role for the muscle in the regulation of oxidation of branched-chain amino acids in the liver, Amino Acids Metabolism and Medical Application. 191-199, 1983.
Paul, Adibi: Mechanism of activation of hepatic branched-chain α-ketoacid dehydrogenase by a muscle factor. J. . Biol. Chem. 258:11471-11475, 1983.
Chicco, Adibi, Liu, Morris, Paul: Regulation of gene expression of branched-chain keto acid dehydrogenase complex in primary cultured hepatocytes by dexamethasone and a cAMP analog. J. Biol. Chem. 269:19427-19434, 1984.
Rodriguez, Schwenk, Beaufrere, Miles, Haymond: Trioctanoin infusion increases in vivo leucine oxidation: a lesson in isotope modeling. Am. J. Physiol. 251: E343-348, 1986.
Vazquez, Paul, Adibi: Relation between plasma and tissue parameters of leucine metabolism in fed and starved rats. Am. J. Phyisol. 250: E615-E621, 1986.
Petroski, Paul, Adibi: Further characterization of a muscle factor which activates hepatic branched-chain ketoacid dehydrogenase. Int. J. Biochem. 18: 979-983, 1986.
Vazquez, Paul, Adibi: Regulation of leucine catabolism by caloric sources: Role of glucose and lipid in nitrogen sparing during nitrogen deprivation. J. Clin. Invest. 82: 1606-1613, 1988.
Vazquez, Paul, Adibi: Leucine catabolism and incorporation into tissue proteins in thyroparathyroidectomized rats. Proc. Soc. Exp. Biol. Med. 187: 33-37, 1988.
Vazquez, Paul, Adibi: Intravenously infused carnitine: influence on protein and branched-chain amino acid metabolism in starved and parenterally fed rats. Am. J. Clin. Nutr. 48: 570-574, 1988.
Imokawa, Abe, Jin, Higaki, Kawashima, Hidano: Decreased level of ceramides in stratum corneum of atopic dermatitia: An etiological factor in atopic dry skin. J. Invest. Dermatol. 96: 523-526, 1991.
Paul, Sekas, Adibi: Investigation of the presence of branched-chain α-keto acid dehydrogenase in mammalian hepatic peroxisomes. Int. J. Biochem. 24: 617-619, 1992.
Paul, Adibi: Mechanism of increased conversion of branched-chain keto acid dehydrogenase from inactive to active form by a medium chain fatty acid (octanoate) in skeletal muscle. J. Biol. Chem. 267:11208-11214, 1992.
Oku, Yagi, Nagata, Chinen: Precursor role of branched-chain amino acids in the biosynthesis of iso and anteiso fatty acids in rat skin. Biochim. Biophys. Acta. 1214: 279-287, 1994.
Mueller, Mckenzie, Homanics, Watkins, Robbins, Paul: Complementation of defective leucine decarboxylation in fibroblasts from a maple syrup urine disease patient by retrovirus-mediated gene transfer: Gene Therapy. 2: 461-468, 1995.
Paul: Regulation of gene expression of the branched-chain keto acid dehydrogenase complex. In: Nutrient and Gene Expression, pp. 21-37, 1996.
Paul, Liu, Adibi: Alteration in gene expression of branched-chain keto acid dehydrogenase kinase but not in gene expression of its substrate in the liver of clofibrate-treated rats. Biochem. J. 317: 411-417, 1996.
Ghadially, Brown, Hanley, Reed, Feingold, Elias: Decreased epidermal lipid synthesis accounts for altered barrier function in aged mice. J. Invest. Dermatol. 106: 1064-1069, 1996.
Lombardo, Thamotharon, Bawani, Paul, Adibi: Posttranscriptional alterations in protein masses of hepatic branched-chain keto acid dehydrogenase and its associated kinase in diabetes. Proc. Assoc. Am. Physicians. 110: 40-49, 1998.
Lombardo, Serdikoff, Thamotharon, Paul, Adibi: Inverse alterations of BCKA dehydrogenase activity in cardiac and skeletal muscles of diabetic rats. Am. J. Physiol. 277: E685-E692, 1999.
Paul, Sekas, Wertz, Grove: A novel metabolic approach to augment the production of skin lipids and improve skin barrier function in humans. Ifscc presentation, 1-5, 2004.
Homanics, Skvorak, Ferguson, Watkins, Paul: Production and characterization of murine models of classic and intermediate maple syrup urine disease. BMC Med. Gen. doi:10.1186/1471-2350-7-33, 2006.
Feingold: The role of epidermal lipids in cutaneous permeability barrier homeostasis, J. Lip. Res. 48: 2531-2546, 2007.
Sugarman: The epidermal barrier in atopic dermatitis. Semin. Cutan. Med. Surg. 27: 108-114, 2008.

* cited by examiner

COMPOSITIONS AND METHODS FOR TREATING DERMATOLOGICAL CONDITIONS

Dermatological conditions are diseases, disorders, symptoms, etc. involving the skin. A non-limiting list of dermatological conditions include atopic dermatitis, allergic contact dermatitis, irritant contact dermatitis, radiation dermatitis, seborrheic dermatitis, psoriasis, sunburn, diabetic ulcers, pressure ulcers, and stasis ulcers. Dermatological conditions can also arise from irritation and/or pain following laser or chemical resurfacing, dermabrasion therapy, cuts, burns, and abrasions. Each dermatological condition, irrespective of cause, is associated with various symptoms, such as erythema, pruritus, exudation, excoriation, and lichenification.

Eczema, or inflammation of the epidermis, pertains to a broad range of dermatological conditions. The most common form of eczema is atopic dermatitis, symptoms of which can include: erythema, pruritus, exudation, excoriation, and lichenification. As yet, there is no cure for most types of dermatitis and most treatments act to ameliorate the symptoms. Treatment for these dermatological conditions varies, which can include the use of corticosteroids, immunosuppression therapies, adoption of life style changes, and the use of various skin care compositions.

Skin care compositions are known to include caprylic acid (also known as octanoate or octanoic acid), either as free acid, but more often in an esterified form as caprylic/capric acid triglycerides. For example, U.S. Pat. No. 5,175,190 discloses a composition for the treatment of skin lesions containing caprylic/capric triglycerides. U.S. Pat. No. 5,569,461 discloses a topical antimicrobial composition containing a monoester of caprylic acid. U.S. Pat. No. 4,760,096 discloses a moisturizing skin preparation containing caprylic/capric acid triglycerides. U.S. Pat. No. 4,495,079 discloses a composition for facial skin cleanser capable of softening and removing sebum plaque containing a mixture of caprylic acid and capric acid esterified to a fatty alcohol. U.S. Pat. No. 5,472,698 discloses the use of several thiol compounds, including the use of lipoic acid in enhancing lipid production in the skin. U.S. Pat. No. 6,149,924 discloses compositions comprising branched-chain amino acids (BCAAs) and their derivatives and optionally medium-chain fatty acids, and a mixture of vitamins and minerals for enhancing lipid production and improving the barrier functions in the mammalian skin.

Currently, treatment of dermatological conditions and symptoms associated with these conditions typically require the use of topical corticosteroid creams to reduce inflammation and itching. However, the long-term use of topical corticosteroids is contraindicated due to potential adverse side effects. Additionally, topical immunomodulating agents, such as tacrolimus and pimecrolimus are used for the management of dermatological conditions. However, such products have been issued a black box warning by the FDA due to possible link with the development of malignancies such as skin cancer and lymphoma. Therefore, a need still exists for a non-corticosteroidal and non-immunomodulators products as long-lasting alternative for the management of symptoms associated with dermatological conditions, such as atopic dermatitis.

SUMMARY

Provided herein are methods of improving one or more symptoms chosen from erythema, pruritus, exudation, excoriation, and lichenification associated with a dermatological condition in a patient, such as a human patient or an animal. The methods comprise topically administering a topical composition to the patient in an amount effective to improve the one or more symptoms in the patient, the topical composition comprising: one or more components selected from the group of L-leucine; L-isoleucine; L-valine; derivatives, metabolites or analogs of L-leucine, L-isoleucine, and L-valine; and a mixture thereof; and one or more enzyme activators selected from the group consisting of caprylic (octanoic) acid, hexanoic acid, alpha keto isocaproic acid, alpha chloroisocaproic acid, thiamin diphosphate, and derivatives or analogs thereof.

Derivatives, metabolites or analogs of L-leucine, L-isoleucine, and L-valine include: nor-leucine; nor-valine; L-alloisoleucine; L-threo-isoleucine; D, L, or DL-serine-containing di- and tri-peptides; D, L, or DL-leucine-containing di- and tri-peptides; D, L or DL-valine-containing di- and tri-peptides; D, L or DL-isoleucine-containing di- and tri-peptides; nitrogen-free analogues of L-leucine, L-isoleucine and L-valine; branched chain keto acids derived from L-leucine, L-isoleucine, and L-valine; isovaleryl-CoA; isovalerylcarnitine; isovalerylglycine; isovaleric acid; beta-methylcrotonyl-CoA, beta-methylcrotonylcarnitine; beta-methylcrotonylglycine; beta-methylcrotonic acid; beta-methylglutaconyl-CoA; beta-methylglutaconylcarnitine; beta-methylglutaconylglycin; beta-methylglutaconic acid; beta-hydroxy-beta-methylglutaryl-CoA; beta-hydroxy-beta-methylglutarylcarnitine; beta-hydroxy-beta-methylglutarylglycine; beta-hydroxy-beta-methylglutaric acid; acetyl-CoA; acetylcarnitine; acetylglycine; acetoacetyl-CoA; acetoacetylcarnitine; acetoacetylglycine; isobutyryl-CoA; isobutyrylcarnitine; isobutyrylglycine; isobutyric acid; methylacrylyl-CoA; methylacrylylcarnitine; methylacrylylglycine; methylacrylic acid; beta-hydroxyisobutyryl-CoA; beta-hydroxyisobutyryl-carnitine; beta-hydroxyisobutyrylglycine; beta-hydroxyisobutyric acid; methylmalonate semialdehyde; propionyl-CoA; propionylcarnitine; propionylglycine; propionic acid; D, L, or DL-methylmalonyl-CoA; D, L, or DL-methylmalonylcarnitine; D, L, or DL-methylmalonylglycine; methylmalonic acid; succinyl-CoA; succinylcarnitine; succinylglycine; succinic acid; alpha-methylbutyryl-CoA; alpha-methylbutyrylcarnitine; alpha-methylbutyrylglycine; alpha-methylbutyric acid; tiglyl-CoA; tiglylcarnitine; tiglylglycine; tiglic acid; alpha-methyl-beta-hydroxybutyryl-CoA; alpha-methyl-beta-hydroxybutyrylcarnitine; alpha-methyl-beta-hydroxybutyrylglycine; alpha-methyl-beta-hydroxybutyric acid; alpha-methylacetoacetyl-CoA; alpha-methylacetoacetylcarnitine; alpha-methylacetoacetylglycine; alpha-methylacetoacetic acid; and mixtures thereof. Derivatives or analogs of caprylic acid, hexanoic acid, alpha keto isocaproic acid, alpha chloroisocaproic acid, and thiamin diphosphate include organic salts; inorganic salts; esters with alcohol or cholesterol; and mono-, di- and triglycerides of caprylic acid or hexanoic acid. In one embodiment, a derivative of caprylic acid is glyceryl caprylate.

The composition may also comprise a vitamin, such as panthenol; pyridoxine; biotin; vitamin E; vitamin A and its derivatives; vitamin $B_1$; vitamin $B_3$; and vitamin C. The composition may also comprise one or more of serine, glycine, alanine and threonine. The composition also optionally may comprise a topical steroid, such as fluocinonide; mometasone furoate; hydrocortisone base or acetate; triamcinolone acetonide; and betamethasone diproprionate The topical steroid may be hydrocortisone base or acetate 0.5-2.5%; triamcinalone acetonide 0.1-0.5%; betamethasone diproprionate 0.05%; fluocinonide 0.05%; triamcinalone acetonide 0.5%; mometasone furoate 0.1%; or betamethasone diproprionate 0.25%, or may be a low strength steroid, such as hydrocortisone base or acetate 0.5%-2.5%. Alternately, the topical steroid may be administered separately from the topical composition. The composition also may comprise a polydimethyl siloxane, such as a dimethicone.

In one non-limiting embodiment, the topical composition comprises L-valine, L-isoleucine, and L-leucine, for example, between 0.025% (% by weight or weight percent) and 0.65% of L-valine, between 0.0075% and 0.20% of L-isoleucine; between 0.015% and 0.35% of L-leucine; between 0.25 and 5.00% of one or more enzyme activators; and between 0.01% and 2.5% of one or more vitamins. In another non-limiting embodiment, the composition comprises: deionized water; biotin; vitamin E; serine; a vitamin B6 (e.g., pyridoxine); panthenol; mono-, di-, tri-glyceryl caprylate; L-valine; L-isoleucine; L-leucine; glycerin; polyoxypropylene-2 myristyl ether propionate; glyceryl stearate/PEG 100 stearate; cetyl alcohol/stearyl alcohol; cyclomethicone; polydimethylsiloxane; stearic acid; one or more plant oils, such as evening primrose (*Oenothera Biennis*) oil, babassu (*Orbignya oleifera*) Oil, avocado (*Persea gratissima*) Oil, safflower (*Carthamus tinctorius*) Oil, olive (*Olea europaea*) oil, or combinations thereof; 2-phenoxyethanol; sodium hydroxymethylglycinate; and disodium EDTA. In another embodiment, the topical composition consists essentially of the ingredients in the ranges stated in Table 1, below. In yet another embodiment, the topical composition consists essentially of the ingredients in the ranges stated in Example 1, below.

In the methods described above for improving one or more symptoms chosen from erythema, pruritus, exudation, excoriation, and lichenification associated with a dermatological condition in a patient, the dermatological condition may be one of atopic dermatitis, allergic contact dermatitis, irritant contact dermatitis, radiation dermatitis, seborrheic dermatitis, psoriasis, sunburn, diabetic ulcers, pressure ulcers, and stasis ulcers. In one embodiment, the Atopic Dermatitis Severity Index is improved in the patient. Because symptoms remain improved well after discontinuation of treatment with the topical composition, one non-limiting embodiment of the method comprises administering the topical composition in a treatment phase in which the topical composition is administered to the patient followed by a regression phase of at least one day in which the topical composition is not administered, but during which time the one or more symptoms remain improved in the patient. In one embodiment, the regression phase is less than 15 days, after which treatment may be resumed, as needed.

In connection with the above methods, a kit is provided for treating a dermatological condition. The kit comprises commercially acceptable packaging, instructions, and a first topical composition comprising in an amount effective to improve erythema, pruritus, exudation, excoriation, and lichenification associated with a dermatological condition in a patient: one or more components selected from the group of L-leucine; L-isoleucine; L-valine; a derivative, metabolite or analog of L-leucine, L-isoleucine, and L-valine; and mixtures thereof; and one or more enzyme activators selected from the group of caprylic acid, hexanoic acid, alpha keto isocaproic acid, alpha chloroisocaproic acid, thiamin diphosphate, and derivatives or analogs thereof. In the kit either: a) the topical composition comprises a topical steroid, or b) a first topical composition comprises a topical steroid, and the kit further comprises a second topical composition that does not comprise a topical steroid (that is, it does not comprise a topical steroid, or essentially or substantially does not comprise a topical steroid, alternately referred to herein as "steroid free"), such that a patient can be treated with an initial treatment of from, e.g., 4-7 days with the composition comprising the topical steroid, and after that time period, the steroid-free composition can be administered. The topical composition may have any composition described above or elsewhere herein.

Also provided are methods of increasing skin moisturization or improving skin barrier function in a dermatological condition having a symptom chosen from one or more of erythema, pruritus, exudation, excoriation, and lichenification. The methods comprise topically administering a topical composition to the patient in an amount effective to improve the one or more symptoms in the patient, the topical composition comprising one or more components selected from the group of L-leucine; L-isoleucine; L-valine; derivatives, metabolites or analogs of L-leucine, L-isoleucine, and L-valine; and a mixture thereof; and one or more enzyme activators selected from the group consisting of caprylic acid, hexanoic acid, alpha keto isocaproic acid, alpha chloroisocaproic acid, thiamin diphosphate, and derivatives or analogs thereof. The topical composition may have any composition described above or elsewhere herein. In one embodiment, the dermatological condition is atopic dermatitis.

Also provided is a topical composition as described herein. For example and without limitation, the topical composition comprises: deionized water; biotin; vitamin E; serine; a vitamin B6 (e.g., pyridoxine); panthenol; mono-, di-, tri-glyceryl caprylate; L-valine; L-isoleucine; L-leucine; glycerin; polyoxypropylene-2 myristyl ether propionate; glyceryl stearate/PEG 100 stearate; cetyl alcohol/stearyl alcohol; cyclomethicone; polydimethylsiloxane; stearic acid; one or more plant oils, such as evening primrose (*Oenothera Biennis*) oil, babassu (*Orbignya oleifera*) Oil, avocado (*Persea gratissima*) Oil, safflower (*Carthamus tinctorius*) Oil, olive (*Olea europaea*) oil, or combinations thereof; 2-phenoxyethanol; sodium hydroxymethylglycinate; and disodium EDTA. In another embodiment, the topical composition consists essentially of the ingredients in the ranges stated in Table 1, below. In yet another embodiment, the topical composition consists essentially of the ingredients in the ranges stated in Example 1, below. In another embodiment, the composition further comprises a topical steroid, such as a low dose topical steroid. Examples of topical steroids include: fluocinonide; mometasone furoate; hydrocortisone base or acetate; triamcinolone acetonide; and betamethasone diproprionate The topical steroid may be hydrocortisone base or acetate 0.5-2.5%; triamcinalone acetonide 0.1-0.5%; betamethasone diproprionate 0.05%; fluocinonide 0.05%; triamcinalone acetonide 0.5%; mometasone furoate 0.1%; or betamethasone diproprionate 0.25%.

Also provided are methods of suppressing reoccurrence in a patient of a symptom associated with a dermatological condition chosen from erythema, pruritus, exudation, excoriation, and lichenification. The methods comprise topically administering a topical composition to the patient in a dosage regimen effective to suppress the one or more symptoms in the patient, the topical composition comprising: one or more components selected from the group of L-leucine; L-isoleucine; L-valine; derivatives, metabolites or analogs of L-leucine, L-isoleucine, and L-valine; and a mixture thereof; and one or more enzyme activators selected from the group consisting of caprylic acid, hexanoic acid, alpha keto isocaproic acid, alpha chloroisocaproic acid, thiamin diphosphate, and derivatives or analogs thereof. In another embodiment, the topical composition consists essentially of the ingredients in the ranges stated in Table 1, below. In yet another embodiment, the topical composition consists essentially of the ingredients in the ranges stated in Example 1, below. In one embodiment, the dermatological condition is atopic dermatitis. In another embodiment, the reoccurrence of the one or more symptoms is suppressed at least one day or from one to 14 days.

DETAILED DESCRIPTION

Figure 1:
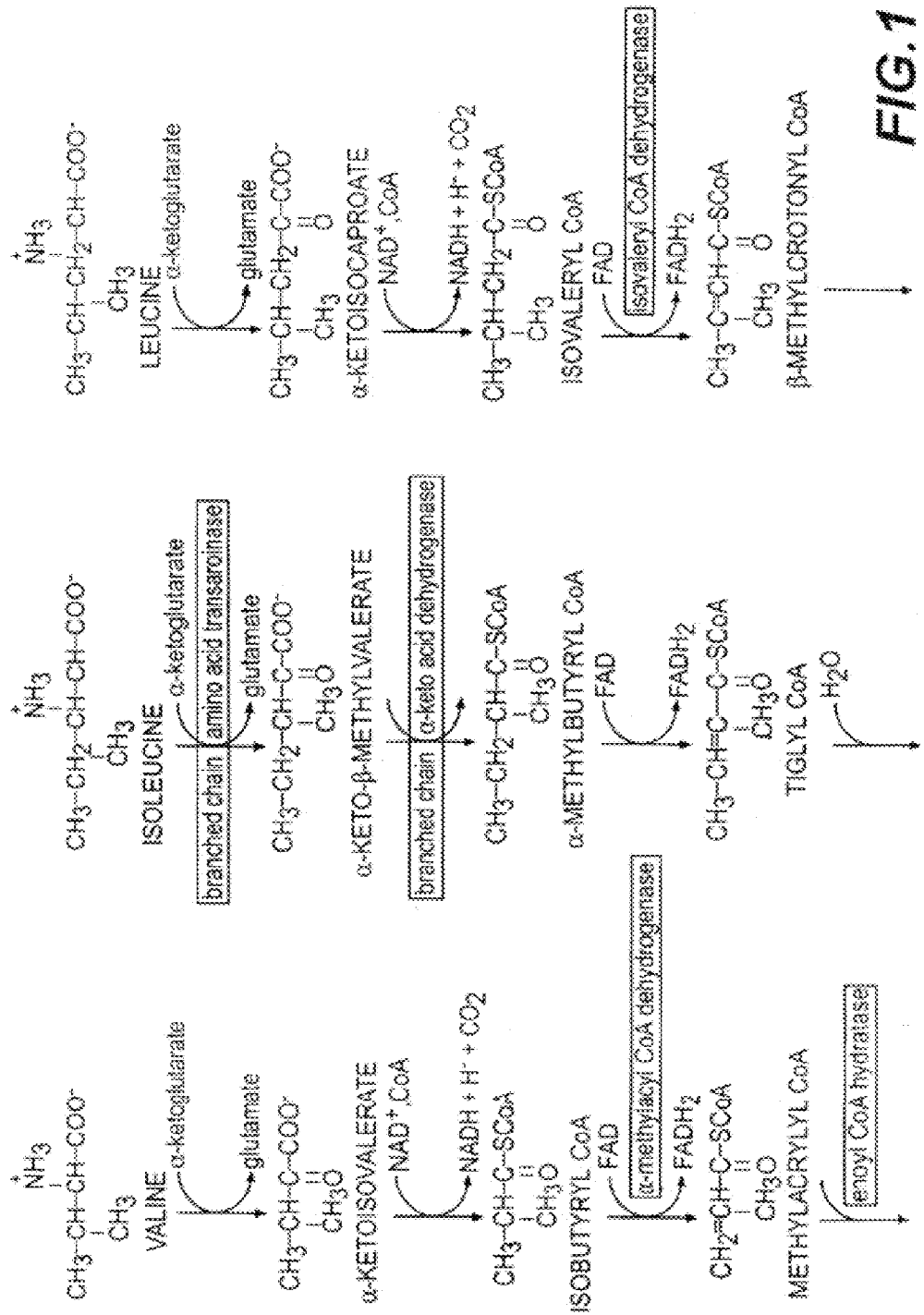
FIG. 1 depicts the metabolic pathway for three preferred branched chain amino acids.
Figure 1:
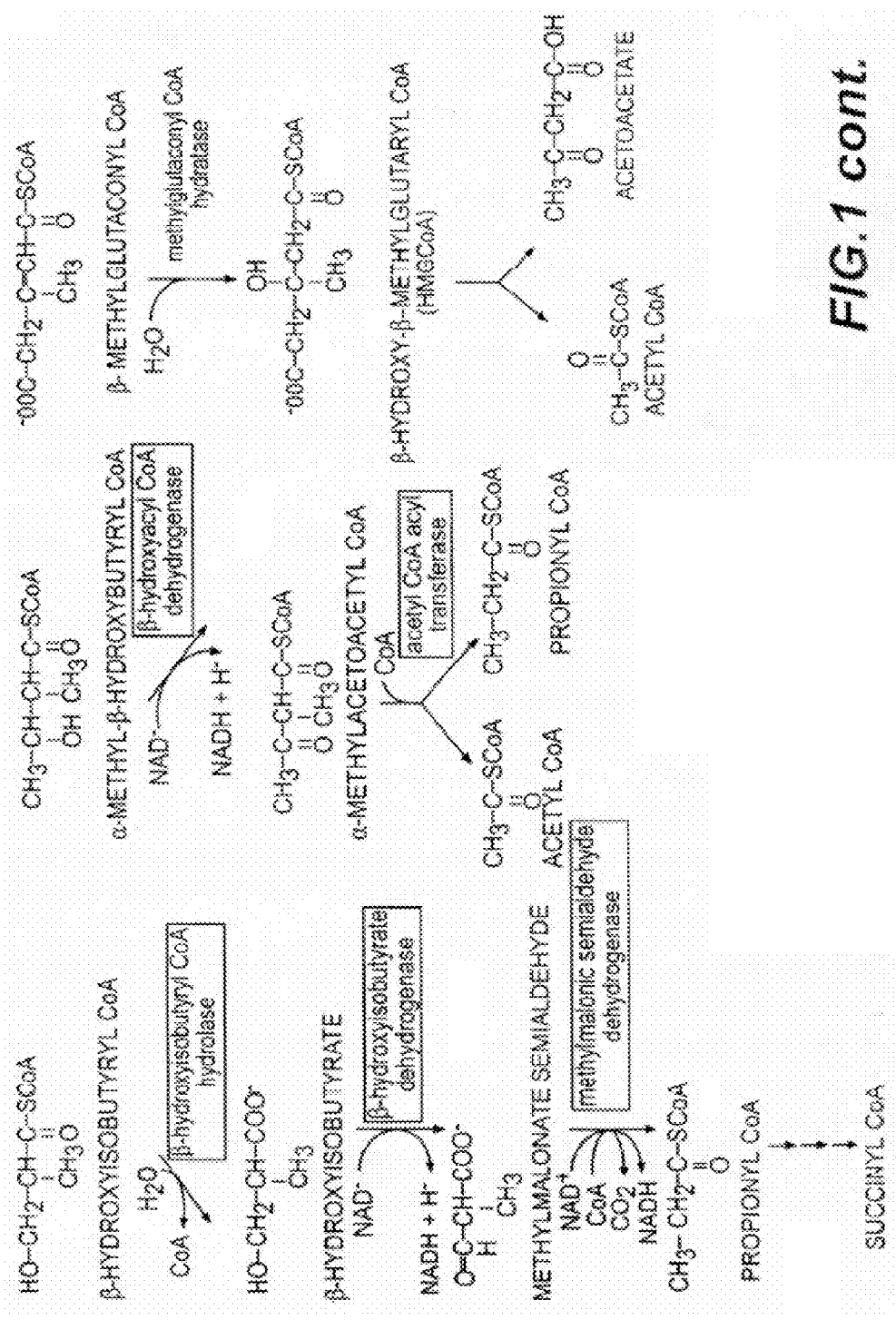

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the term "patient" refers to members of the animal kingdom including but not limited to mammals and human beings and is not limited to humans or animals in a doctor-patient or veterinarian-patient relationship. A patient includes a pediatric patient. The topical composition described herein may have a particular benefit to pediatric patients, where use of steroids is contraindicated.

The topical composition can be used to treat dermatological condition. As used herein, the term "dermatological condition" refers to any condition relating to diseased and/or damaged skin. Non-limiting examples of dermatological conditions include atopic dermatitis, allergic contact dermatitis, irritant contact dermatitis, radiation dermatitis, seborrheic dermatitis, psoriasis, sunburn, diabetic ulcers, pressure ulcers, and stasis ulcers. Dermatological conditions can also arise from irritation and/or pain following laser or chemical resurfacing, dermabrasion therapy, cuts, burns, and abrasions.

Therefore, as described above, methods are provided for improving one or more symptoms chosen from erythema, pruritus, exudation, excoriation, and lichenification associated with a dermatological condition in a patient, such as a human patient or an animal. The methods comprise topically administering a topical composition to the patient in an amount effective to improve the one or more symptoms in the patient. The topical composition is described herein. In the methods, the dermatological condition may be one of atopic dermatitis, allergic contact dermatitis, irritant contact dermatitis, radiation dermatitis, seborrheic dermatitis, psoriasis, sunburn, diabetic ulcers, pressure ulcers, and stasis ulcers. In one embodiment, the Atopic Dermatitis Severity Index is improved in the patient.

Because symptoms remain improved well after discontinuation of treatment with the topical composition, one non-limiting embodiment of the method comprises administering the topical composition in a treatment phase in which the topical composition is administered to the patient followed by a regression phase of at least one day in which the topical composition is not administered, but during which time the one or more symptoms remain improved in the patient. In one embodiment, the regression phase is less than 15 days, after which treatment may be resumed, as needed. Also provided are methods of suppressing reoccurrence in a patient of a symptom associated with a dermatological condition chosen from erythema, pruritus, exudation, excoriation, and lichenification, comprising topically administering a topical composition as described herein to the patient in a dosage regimen effective to suppress the one or more symptoms in the patient. In one embodiment, the dermatological condition is atopic dermatitis. In another embodiment, the reoccurrence of the one or more symptoms is suppressed at least one day or longer or, alternately, from one to 14 days. In one embodiment, reoccurrence is suppressed if one or more testable parameters, such as ADSI or other end-point(s), is/are improved at least 5%, 10%, 15%, 20%, 25% or more, including increments therebetween, as compared to a pretreatment measurement for the testable parameter (see, e.g., Tables 9, 10, and 12-14.

Also provided is a method of increasing skin moisturization or improving skin barrier function in a dermatological condition having a symptom chosen from one or more of erythema, pruritus, exudation, excoriation, and lichenification. The method comprises topically administering a topical composition as described herein to the patient in an amount effective to improve the one or more symptoms in the patient.

As used herein, the "treatment" or "treating" of a dermatological condition means administration to a patient by any suitable dosage regimen of a topical composition with the object of improving (e.g., ameliorating, alleviating, delaying, suppressing, reducing and/or normalizing) any symptom, indicator, lesion, etc. associated with the dermatological condition, including, without limitation, any testable parameter, whether or not subjective, such as, without limitation, pain levels, or objective, such as, without limitation, lesion size. Without wishing to be limited by theory, the topical composition is applied to diseased and/or damaged skin to relieve the symptoms by forming a protective barrier and maintaining a moist skin environment to benefit the healing process. Non-limiting examples of symptoms include erythema or redness in the affected skin area; pruritus or itching in the affected skin area; exudation or oozing and/or crusting in the affected skin area; excoriation or evidence of scratching in the affected skin area; and lichenification or epidermal thickening in the affected skin area.

In one non-limiting example, the testable parameter associated with assessing the dermatological condition is the Atopic Dermatitis Severity Index ("ADSI", see Example 2, below). ADSI provides for a summary score that relies on five clinical features of atopic dermatitis, including erythema, pruritus, exudation, excoriation, and lichenification. These five clinical features are typically assessed on each patient's selected target lesion using a four-point scale system. As used herein, an ADSI is improved in a patient when the index is improved after treatment with a topical composition results as compared to before the treatment. For example and without limitation, an ADSI is improved in a patient, where the ADSI was 6.75 before treatment and the ADSI was 4.75 two weeks after treatment.

The topical composition can be administered in any dosage regimen useful to treat a dermatological condition. A dosage regimen is a treatment protocol for a patient, for instance including the amount of a drug product administered to the patient, the number of doses administered to the patient, and the time period over which the doses are administered to the patient. As non-limiting examples of dosage regimens, the topical composition is topically administered to a patient from one to six times daily to an area of the patient's skin affected by the dermatological condition for from one day to a year or more, or any increment therebetween, such as for one, two, four, eight, ten, 12 or more weeks, or, optionally, as-needed.

The methods described herein may be used in combination with other therapy to treat a dermatological condition. For example and without limitation, methods also are provided that comprise topically administering a topical steroid before or after topically administering the topical composition. In another non-limiting example, the method comprises topically administering a topical steroid in conjunction with topically administering the topical composition. The therapies can be combined in any useful way to provide therapeutic benefit for a patient with a dermatological condition. For example and without limitation, the method comprises topically administering a low-dose topical steroid for a period of from one to five days before topically administering the topical composition.

The topical composition comprises one or more of L-leucine, L-isoleucine, L-valine, and derivatives, metabolites or analogs of L-leucine, L-isoleucine, and L-valine or mixtures thereof, and one or more enzyme activators. As used herein, the terms "components" and "component" refer to one or more of L-leucine, L-isoleucine, L-valine, and derivatives, metabolites or analogs of L-leucine, L-isoleucine, and L-valine or mixtures thereof. Without wishing to be limited by theory, the components typically comprise branched chain amino acids capable of being catabolized into small carbon fragments which then are used for the synthesis and production of skin lipids, fortify the skin barrier, enhance its recovery rate, and provide prolonged and therapeutic moisturization to the skin. Without wishing to be limited by theory, the role of serine is to serve as a building block for the production of skin ceramides, which maintain barrier function of the skin.

Figure 2:
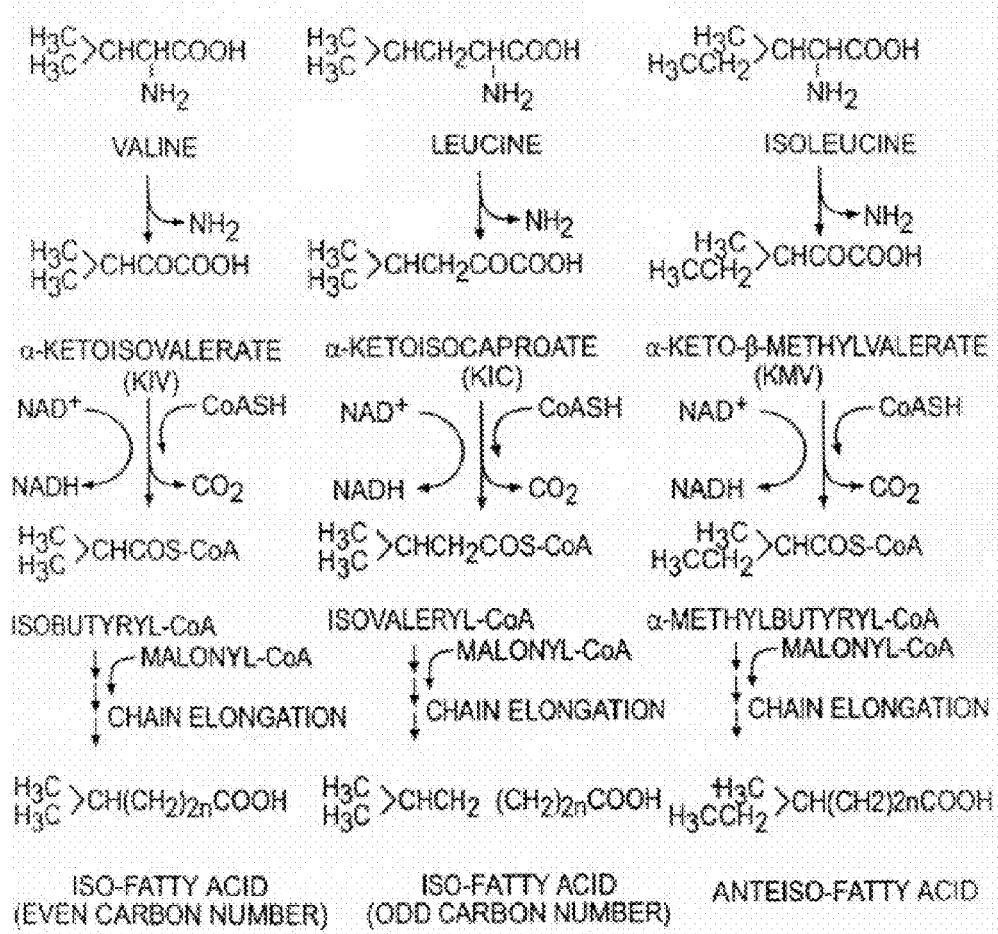
FIG. 2 depicts the synthesis of branched-chain fatty acids from the metabolites of three preferred branched-chain amino acids.

Metabolites are intermediate products of a substrate along its metabolic pathway and, in the context of the present disclosure, as indicated for example in FIGS. 1 and 2, include compounds like isobutyrl-CoA, tiglyl-CoA, isovaleryl-CoA, etc. Analogs are compounds with a slightly altered chemical structure as compared to a parent compound and, in the present context, include compounds like α-ketoisovalerate, α-ketoisocaproate, α-keto-β-methylvalerate, etc. Analogs often differ from a parent or reference compound by substitution of groups with similar, groups (e.g., similar size, charge, hydrophobicity, etc.) that in cosmetic and/or pharmacological use, often have identical or similar efficacy in their use and are common. For example, one halide may be substituted for another, a double bond may be replaced with a single bond (or vice versa), hydrogens and methyl, ethyl or propyl groups may be interchangeable, =O and =S may be interchangeable, —$NO_2$ and —$CO_2$ groups may be interchangeable, or N, O or S atoms in a heterocyclic ring may be substituted for one-another. Analogs include isosteres of the parent compounds, which are molecules or ions with the same number of atoms and the same number of valence electrons. As a result, they can exhibit similar pharmacokinetic and pharmacodynamic properties. "Derivatives" can be analogs that have been derived conceptually and/or chemically from a parent compound, but also comprise more substantial changes that are substantially inert in that they do not affect function negatively, such as PEGylation, conversion to a pharmaceutically acceptable salt, or other modifications.

The topical compositions described herein contain precursors of lipids. These precursors include a group of lipogenic amino acids, such as branched chain amino acids and their derivatives, metabolites or analogs. In addition, the composition may contain enzyme activators and vitamins to accelerate the metabolism of these amino acids and increase the production of precursors of skin lipids. All of the ingredients of the topical compositions, being of relatively low molecular weight, readily penetrate into the skin, many of which are utilized for lipid production using the biochemical machinery of the skin cells.

Lipogenic amino acids include branched chain amino acids capable of being catabolized into small carbon fragments which are used for the synthesis of fatty acids and cholesterol. Skin cells have the capacity to transport and degrade branched-chain amino acids into small fragments. These carbon fragments then serve as precursors ("pro-lipids") for skin lipid synthesis. Acyl-CoA intermediates derived from branched-chain amino acids can serve as a "primer" or "starter" for the synthesis and chain elongation of fatty acids found in skin lipids. The fatty acid chain is elongated by adding to the "starter" CoA derivative a number of $C_2$ units. These $C_2$ units are derived from malonyl-CoA as shown in FIG. 2 and described in Nicolaides: Science, 186: 19-26, 1974. The amino acids can be used either in their levorotary (L), dextrorotary (D), or racemic (DL) forms.

BCAAs include one or more L-leucine, L-valine, L-isoleucine, and mixtures thereof. Besides the branched-chain amino acids, derivatives, metabolites or analogs of those amino acids can also be used. Non-limiting examples of derivatives, metabolites or analogs of L-leucine, L-isoleucine, and L-valine include: nor-leucine; nor-valine; L-alloisoleucine; L-threo-isoleucine; D, L, or DL-serine-containing di- and tri-peptides; D, L, or DL-leucine-containing di- and tri-peptides; D, L or DL-valine-containing di- and tri-peptides; D, L or DL-isoleucine-containing di- and tri-peptides; nitrogen-free analogues of L-leucine, L-isoleucine and L-valine; branched chain keto acids derived from L-leucine, L-isoleucine, and L-valine; isovaleryl-CoA; isovalerylcarnitine; isovalerylglycine; isovaleric acid; beta-methylcrotonyl-CoA, beta-methylcrotonylcarnitine; beta-methylcrotonylglycine; beta-methylcrotonic acid; beta-methylglutaconyl-CoA; beta-methylglutaconylcarnitine; beta-methylglutaconylglycin; beta-methylglutaconic acid; beta-hydroxy-beta-methylglutaryl-CoA; beta-hydroxy-beta-methylglutarylcarnitine; beta-hydroxy-beta-methylglutarylglycine; beta-hydroxy-beta-methylglutaric acid; acetyl-CoA; acetylcarnitine; acetylglycine; acetoacetyl-CoA; acetoacetylcarnitine; acetoacetylglycine; isobutyryl-CoA; isobutyrylcarnitine; isobutyrylglycine; isobutyric acid; methylacrylyl-CoA; methylacrylylcarnitine; methylacrylylglycine; methylacrylic acid; beta-hydroxyisobutyryl-CoA; beta-hydroxyisobutyrylcarnitine; beta-hydroxyisobutyrylglycine; beta-hydroxyisobutyric acid; methylmalonate semialdehyde; propionyl-CoA; propionylcarnitine; propionylglycine; propionic acid; D, L, or DL-methylmalonyl-CoA; D, L, or DL-methylmalonylcarnitine; D, L, or DL-methylmalonylglycine; methylmalonic acid; succinyl-CoA; succinylcarnitine; succinylglycine; succinic acid; alpha-methylbutyryl-CoA; alpha-methylbutyrylcarnitine; alpha-methylbutyrylglycine; alpha-methylbutyric acid; tiglyl-CoA; tiglylcarnitine; tiglylglycine; tiglic acid; alpha-methyl-beta-hydroxybutyryl-CoA; alpha-methyl-beta-hydroxybutyrylcarnitine; alpha-methyl-beta-hydroxybutyrylglycine; alpha-methyl-beta-hydroxybutyric acid; alpha-methylacetoacetyl-CoA; alpha-methylacetoacetylcarnitine; alpha-methylacetoacetylglycine; alpha-methylacetoacetic acid; and mixtures thereof.

L-leucine, L-valine, and L-isoleucine, branched-chain amino acids, serve as precursors for lipid synthesis. Catabolism of these branched-chain amino acids results in the production of small carbon fragments which are efficiently utilized for the synthesis of fatty acids and cholesterol.

Besides the branched-chain amino acids, the non-essential amino acid serine (or its derivative such as serine-containing dipeptides) may also be used in the present invention. The role of serine or its analogs is to serve as a building block for the production of skin ceramides. Serine by reacting with palmitoyl-CoA is converted into 3-ketosphingosine, which through a series of reactions is converted into ceramides. Skin cells are capable of converting serine into ceramides. Another advantage of serine is that in the skin, it is metabolized to pyruvate which then produces acetyl-CoA for lipid synthesis.

Optionally, the composition may also contain the amino acids glycine, alanine, and threonine. Glycine is converted in the skin to serine, which as noted above serves as a building block for the production of skin ceramides. Alanine is converted in the skin to pyruvate, which as noted above, is used in the production of acetyl-CoA. Threonine is converted in the skin to alpha-ketobutyrate which is useful in acidifying the skin and neutralizing $H_2O_2$. Furthermore, the alpha-ketobutyrate is metabolized to propionyl-CoA which is used in the production of lipids.

L-leucine, L-valine, and L-isoleucine are also believed to have an indirect role in the synthesis of ceramides. As described above, skin is capable of synthesizing a large variety of branched-chain fatty acids utilizing the branched-chain amino acids. Some of these fatty acids have the potential to be incorporated into skin ceramides. The biosynthesis of ceramide in the skin is a two step process. It begins with a reaction between palmitoyl-CoA and the non-essential amino acid, serine. This reaction is catalyzed by the enzyme, serine palmitoyltransferase. The resulting product is 3-ketosphingosine, which then is reduced to form dihydro sphingosine (also known as sphinganine). Next, the addition of an amide-linked fatty acid results in ceramide. It appears that the synthesis of sphingosine in the skin may not be very diligently controlled. A variety of long-chain fatty acyl-CoAs, including the branched-chain fatty acyl-CoAs, can be substituted for palmitoyl-CoA. Thus, branched-chain amino acids have the potential to contribute to the formation of sphingosine. In the second step of ceramide synthesis, fatty acids of varying chain length are utilized for acylation of sphingosine. Branched-chain fatty acids can be substituted for other fatty acids for this acylation reaction. Thus branched-chain amino acids have the possibility of contributing to the amide-linked fatty acid of ceramides. In summary, branched-chain amino acids can contribute to ceramide production in the skin.

L-leucine, L-valine, and L-isoleucine are readily transported into the skin cells. Although not intending to be bound by any theory, it is believed that in the cell, these amino acids undergo a transamination reaction which results in the formation of branched-chain keto acids, as shown in FIG. 1. These keto acids comprise alpha ketoisocaproic acid, alpha keto beta methylvaleric acid and alpha ketoisovaleric acid derived from leucine, isoleucine, and valine, respectively. In the next step, all three branched-chain keto acids are oxidatively decarboxylated by a single mitochondrial multienzyme complex known as branched-chain keto acid dehydrogenase. The reaction products of alpha ketoisocaproic acid, alpha keto beta methylvaleric acid, and alpha keto isovaleric acid are isovaleryl-CoA, alpha methylbutyryl-CoA, and isobutyryl-CoA, respectively. These branched-chain acyl-CoAs further undergo a series of biochemical reactions that result in the production of small carbon fragments. The final end products of leucine catabolism are a two carbon acetyl-CoA and a four carbon acetoacetic acid. Acetoacetic acid is further metabolized to yield two molecules of acetyl-CoA. The final end products of isoleucine catabolism are acetyl-CoA and a three carbon propionyl-CoA. Further metabolism of propionyl-CoA results in four carbon succinyl-CoA, which is an intermediate of Krebs cycle. Further metabolism of succinyl-CoA results in citric acid formation. The final end product of valine catabolism is propionyl-CoA, which then is metabolized to succinyl-CoA.

All the intermediate products of branched-chain amino acid metabolism are excellent precursors for fatty acid and cholesterol synthesis. Additionally, one of the intermediates in the leucine catabolic pathway, beta-hydroxy-beta-methyl glutaryl-CoA, is efficiently converted into cholesterol.

Besides utilizing BCAAs for synthesis of lipids in the epidermis, BCAAs are also utilized for the synthesis of lipids in the sebaceous glands. The sebaceous glands utilize BCAAs to synthesize branched-chain fatty acids (BCFA), which then become part of the sebum. Secretion of BCFA-enriched sebum on the skin surface may prevent dehydration of the skin.

Another advantage and use of BCAAs is as follows. A naturally occurring potent moisturizing component known as Natural Moisturizing Factor (NMF) is found in the stratum corneum. NMF serves as an efficient moisturizer because its constituent chemicals are highly water soluble, hygroscopic, and very efficient humectants. It is now well recognized that NMF is a mixture of amino acids and their derivatives. Therefore, BCAAs and their numerous derivatives, metabolites or analogs may increase NMF's constituent chemical pool and thus aid in the skin's moisturization.

Since the metabolism of BCAA is coupled with the production of alanine, glutamic acid and glutamine in the skin, these amino acids thus can further contribute to increasing the levels of NMF constituents. Additionally, glutamine in the skin is converted to pyrrolidone carboxylic acid, a highly potent humectant.

Another relationship between BCAAs, skin barrier, and NMF is that a stronger barrier will prevent the loss of NMF from the skin, and thus allows maximum moisturization of the skin.

The total amount of each of the one or more of L-leucine, L-isoleucine, L-valine, derivatives, metabolites or analogs of L-leucine, L-isoleucine, and L-valine, and mixtures thereof in the topical composition generally ranges from 0.001% to 40 wt %, acceptably from 0.01% to 20 wt %, and also acceptably from 0.01% to 10 wt %. However, other concentrations are acceptable, e.g., 0.1 to 5, 0.5 to 5, 1 to 3, 3 to 5, 5 to 7, 10 to 15, 15 to 20 and >20 wt %. The compounds L-leucine, L-isoleucine, L-valine, or derivatives, metabolites or analogs of L-leucine, L-isoleucine, and L-valine may be used individually or in combinations of two or more of the compounds. When more than one branched-chain amino acids are used, the ratio and proportions between them can be varied in order to maximize their metabolic potential as lipid precursors. For example, when L-isoleucine, L-leucine, and L-valine are used, an acceptable range of weight ratios between L-isoleucine, L-leucine and L-valine is (0.5-1.5):(1-3):(2-6), respectively, for instance, a ratio of 1:2:4, respectively.

Figure 3:
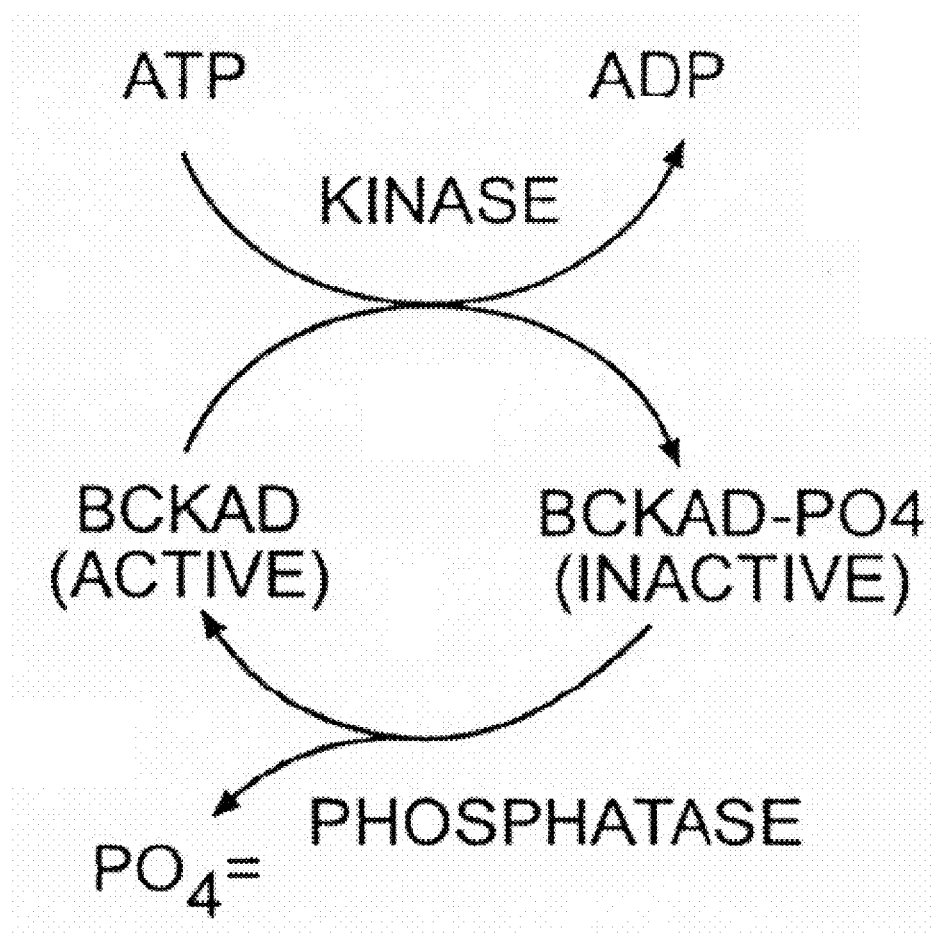
FIG. 3 depicts the inactivation and activation of branched-chain keto acid (BCKA) dehydrogenase (BCKDH) by phosphorylation and dephosphorylation, respectively.

The catabolism of branched-chain amino acids is highly regulated. The rate-limiting step for the catabolism of these amino acids is the enzyme branched-chain keto acid dehydrogenase. The activity of this enzyme acts as a "bottle-neck" in the pathway that leads to the production of lipid synthesizing precursors from branched-chain amino acids. In most cells, branched-chain keto acid dehydrogenase exists in two forms, an active, dephosphorylated form, and an inactive, phosphorylated form. Phosphorylation and inactivation of branched-chain keto acid dehydrogenase is catalyzed by a specific protein kinase as shown in FIG. 3. The proportion of branched-chain keto acid dehydrogenase in the active, dephosphorylated form varies among various tissues. Only in the active form, the branched-chain keto acid dehydrogenase is capable of catabolizing the branched-chain amino acids.

Those tissues in which branched-chain keto acid dehydrogenase exists largely in an inactive, phosphorylated form, is due to the presence of a large amount of the kinase in these tissues. For example, in the skeletal muscle, a tissue in which branched-chain keto acid dehydrogenase exists largely in an inactive form, there is a high kinase activity. On the other hand, in the liver, where branched-chain keto acid dehydrogenase exists largely in an active form, there is very little kinase activity. Scientific studies have shown that in those tissues where branched-chain keto acid dehydrogenase exists in an inactive or only partially active form, this enzyme can be converted into a fully active form by kinase inhibitors such as the medium-chain fatty acid octanoate (Paul: J. Biol. Chem. 267: 11208-11214, 1992). Inhibition of the kinase blocks the phosphorylation of branched-chain keto acid dehydrogenase, thus maintaining this enzyme into its active form. The net effect is that a fully active form of branched-chain keto acid dehydrogenase can now catabolize branched-chain amino acids at a much faster rate.

In the human skin fibroblasts, approximately 35% of the branched-chain keto acid dehydrogenase exists in the active, dephosphorylated, form (Toshima et. al.: Clin. Chim. Acta 147: 103-108, 1985). This means that under normal metabolic conditions, only a small fraction of the available branched-chain amino acids can be converted into lipid precursors. In order to maximize the production of such precursors from branched-chain amino acids, it is essential to convert branched-chain keto acid dehydrogenase into a fully active form. This can be accomplished by including an enzyme activator, such as octanoate in the topical composition described herein. Octanoate readily penetrates into the skin and inhibits the phosphorylation of the branched-chain keto acid dehydrogenase, which results in increased activity of this enzyme. This in turn stimulates catabolism of branched-chain amino acids. The net effect of these changes is increased production of small carbon fragments from branched-chain amino acids, which then are utilized for skin lipid synthesis.

As used herein, the terms "enzyme activators" and "enzyme activator" refer to one or more of caprylic acid, hexanoic acid, alpha keto isocaproic acid, alpha chloroisocaprioc acid, thiamin diphosphate, derivatives or analogs thereof. Without wishing to be limited by the theory, the enzyme activators disclosed herein promote the catabolism of the BCAA(s) by activating the enzyme branched-chain keto acid dehydrogenase. For example, scientific studies have shown that in those tissues where branched-chain keto acid dehydrogenase exists in an inactive or only partially active form, this enzyme can be converted into a fully active form by kinase inhibitors such as the medium-chain fatty acid octanoate (Paul: J. Biol. Chem. 267: 11208-11214, 1992). In order to maximize the production of such precursors from branched-chain amino acids, the branched-chain keto acid dehydrogenase could be converted into a fully active form. This can be accomplished by including enzyme activator(s) in the composition of the present invention. For example and without limitation, octanoate readily penetrates into the skin and inhibits the phosphorylation of the branched-chain keto acid dehydrogenase, which results in increased activity of this enzyme and stimulation of the catabolism of branched-chain amino acids. The net effect of these changes is increased production of small carbon fragments from branched-chain amino acids, which then are utilized for skin lipid synthesis. Some BCAAs, in particular, L-leucine, have been found to have an enzyme activation effect. However, this effect is significantly less in comparison to the activators listed herein. Accordingly, enzyme activators do not include BCAAs.

Non-limiting examples of derivatives or analogs of caprylic acid, hexanoic acid, alpha keto isocaproic acid, alpha chloroisocaproic acid, and thiamin diphosphate include: organic salts; inorganic salts; esters with alcohol or cholesterol; and mono-, di- and triglycerides of caprylic acid or hexanoic acid (glyceryl caprylate). In one non-limiting embodiment, the derivative of caprylic acid is an ester of caprylic acid. For example and without limitation, the ester of caprylic acid is glyceryl caprylate. The derivatives can include organic salts (e.g., ornithine salts), inorganic salts (e.g., sodium and potassium salts), esters with alcohol or cholesterol, and mono-, di- and triglycerides of caprylic acid or hexanoic acid.

Derivatives of caprylic acid, hexanoic acid, alpha keto isocaproic acid, alpha chloroisocaprioc acid can also be formed by reacting one or more enzyme activators with an alcohol or cholesterol to form an ester. Non-limiting examples of alcohols include alkyl alcohols, such as $C_1$-$C_{10}$ linear and branched alcohols; and polyols, such as ethylene glycol, glycerol. Non-limiting examples of derivatives include mono-, di- and triglycerides of caprylic acid, hexanoic acid, alpha keto isocaproic acid, and alpha chloroisocaproic acid.

The enzyme activator octanoate may also have other roles. For example, besides functioning as an activator of the branched-chain keto acid dehydrogenase, this fatty acid itself can be incorporated into skin lipids (Adv. Lip. Res. 24: 57-82, 1991). Octanoate can be incorporated into skin lipid by first being converted to octanoyl-CoA and its subsequent metabolism to acetyl-CoA, which then can be used for cholesterol and fatty acid synthesis. Another potential benefit of octanoate in the present invention is that it improves the moisturization of the skin.

The amount of enzyme activator can also be varied depending upon the concentration of component(s) in the formulation of the topical composition. In general, the total amount of enzyme activator ranges from 0.001% to 20%, acceptably from 0.01% to 10%, and also acceptably from 0.1% to 5%. However, other concentrations are acceptable, e.g., 0.1 to 5, 0.5 to 1.0, 1 to 3, 3 to 5, 5 to 7, 10 to 15, 15 to 20 and >20 wt %.

Pharmaceutically acceptable organic and inorganic salt forms of any of the compounds or compositions described herein, such as of the derivatives or analogs of caprylic acid, hexanoic acid, alpha keto isocaproic acid, alpha chloroisocaprioc acid, and thiamin diphosphate may be prepared by conventional methods known in the pharmaceutical arts. For example and without limitation, where the compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

As used herein, an "amount effective" means an amount of the topical composition to treat a dermatological condition. The topical composition comprises one of more of L-leucine, L-isoleucine, L-valine, derivatives of L-leucine, L-isoleucine, and L-valine, and mixtures thereof, one or more enzyme activators, and one or more vitamins in any useful combination. For example and without limitation, a topical composition in an amount effective to improve one or more of erythema, pruritus, exudation, excoriation, and lichenification comprises ranges of one or more of L-leucine, L-isoleucine, L-valine, derivatives, metabolites or analogs of L-leucine, L-isoleucine, and L-valine, and mixtures thereof, as shown in Table 1.

As used herein, the terms "vitamins" and "vitamin" refer to one or more of panthenol (vitamin $B_5$); pyridoxine (vitamin $B_6$); biotin ((vitamin H); vitamin E; vitamin A and its derivatives, such as retinol and retinoic acid; vitamin $B_1$ (thiamin); vitamin $B_3$; and vitamin C. Without wishing to be limited by theory, vitamins typically serve as cofactors for many biochemical reactions involving branched-chain amino acid metabolism.

Besides branched-chain amino acids, the non-essential amino acid serine (or its derivatives such as serine-containing dipeptides) may also be used in the topical composition of the methods, compositions and kits described herein. The role of serine or its derivatives is to serve as a building block for the production of skin ceramides. Serine by reacting with palmitoyl-CoA is converted into 3-ketosphingosine, which through a series of reactions is converted into ceramides. Skin cells are capable of converting serine into ceramides. Another advantage of serine is that in the skin, it is metabolized to pyruvate which then produces acetyl-CoA for lipid synthesis.

The composition may also contain one or more of the amino acids glycine, alanine and threonine. Glycine is converted in the skin to serine, which, as noted above, serves as a building block for the production of skin ceramides. Alanine is converted in the skin to pyruvate, which as noted above, is used in the production of acetyl-CoA. Threonine is converted in the skin to alpha-ketobutyrate which is useful in acidifying the skin and neutralizing $H_2O_2$. Furthermore, the alpha-ketobutyrate is metabolized to propionyl-CoA which is used in the production of lipids.

Other optional ingredients which may be advantageously employed include one or more vitamins. The majority of people in the U.S. consume diets that fall short of the recommended daily allowances for most vitamins. Such deficient diets make skin cells also deficient with these vitamins and compromise their ability to perform normal metabolism. In general, vitamins are essential for good health and protect the skin cells from damage caused by natural body processes (free radical production), lifestyles (smoking), and environmental stress (chemical pollutants and UV radiation) and aging and photodamaging. Vitamins usable with the present invention can include one or more of panthenol, pyridoxine, biotin, vitamin E, and mixtures thereof.

One role of vitamins in the topical compositions described herein is to serve as cofactors for many biochemical reactions of branched-chain amino acid metabolism and for reactions necessary for lipid production. Useful vitamins include vitamin $B_5$ (panthenol), vitamin $B_6$ (pyridoxine), vitamin H (biotin), and vitamin E. The vitamins are incorporated into the formulation in any suitable form.

Vitamin $B_5$ (panthenol) is included as a stable and biologically active analog of pantothenic acid, a vitamin of the B-complex group and a normal constituent of the skin and hair. When panthenol is applied topically, it quickly penetrates into the skin, is readily converted into pantothenic acid, and is incorporated into CoA. Pantothenic acid improves wound repair and healing. This is due to the effect of pantothenic acid on intracellular protein synthesis and cell proliferation. Thus, it may play a role in the aging skin. Panthenol is a water soluble, non-irritating, and non-sensitizing moisturizing agent. The humectant character of panthenol enables it to hold water or attract water from the environment to yield moisturizing effects to the skin and thus prevents dry skin. Deficiency of pantothenic acid in laboratory animals causes dermatitis.

The role of panthenol in the topical compositions is several fold. First and foremost, the CoA derived from panthenol aids in the conversion of branched-chain keto acids into their respective acyl-CoA derivatives. CoA is necessary to activate acetate and palmitate to acetyl-CoA and palmitoyl-CoA, respectively. Acetyl-CoA will serve as a substrate for cholesterol and fatty acid synthesis while palmitoyl-CoA will react with serine to initiate the process of ceramide synthesis. Besides the above functions, CoA has several other roles in cellular metabolism. It plays a role in fatty acid metabolism, and in the synthesis of cholesterol, lipids, and proteins. More than 70 enzymes utilize CoA in a variety of metabolic reactions. Additionally, pantothenic acid is a component of phosphopantetheine of fatty acid synthetase, an enzyme important for the synthesis of intracellular lipids (Devlin: Textbook of Biochemistry, 3rd edition, 28:1132, 1992). Taken together, there are many beneficial reasons for including panthenol (vitamin $B_5$) in the composition of the present invention.

Vitamin $B_6$ (e.g., pyridoxine) is metabolized intracellulary to pyridoxal phosphate, the coenzyme form of this vitamin. In this form, it functions as a cofactor for several biochemical reactions. Pyridoxine is utilized as a cofactor by more than 60 enzymes. Pyridoxine aids in amino acid metabolism, particularly in the transaminase reaction of the amino acids, including the transamination of branched-chain amino acids. Additionally, pyridoxine plays a role in the synthesis, catabolism, and interconversion of amino acids. Thus, it is essential for the metabolism of nearly all amino acids. In the present invention, the main function of pyridoxine is to facilitate the transamination of branched-chain amino acids, an important first step for their metabolism. Additionally, this vitamin functions as a coenzyme for the serine-palmitoyl-CoA transferase, the rate-limiting enzyme for the synthesis of ceramides in the skin (Devlin: Textbook of Biochemistry, 3rd edition, 10:449-456, 1992). An additional advantage of including pyridoxine is that this vitamin is involved in the production of niacin from the amino acid tryptophan. Niacin and its coenzymes nicotinamide adenine dinucleotide (NAD and NADH) and nicotinamide adenine dinucleotide phosphate (NADP and NADPH) are important cofactors for both amino acid and fatty acid metabolism.

The vitamin biotin functions as a cofactor for carboxylation reactions. Thus, this vitamin plays an important role in fatty acid and amino acid metabolism. There are several carboxylation steps in the catabolism of branched-chain amino acids which require biotin. In fact, deficiency of biotin has been shown to disturb the metabolism of leucine, one of the branched-chain amino acids, in laboratory animals (J. Nutr. 122: 1493-1499, 1992). The role of biotin in the present invention is several fold. It is included to serve as a cofactor for a number of carboxylases, such as 3-methylcrotonyl-CoA carboxylase in the leucine catabolic pathway, propionyl-CoA carboxylase in the valine catabolic pathway, and acetyl-CoA carboxylase, the rate-limiting enzyme for fatty acid synthesis. Additionally, biotin is a cofactor for the enzyme pyruvate carboxylase. Through its role in pyruvate carboxylase, biotin is essential for the replenishment of the citric acid cycle metabolites which are essential for normal cellular functions.

Vitamin E may be included because of its antioxidant properties and its ability to neutralize free radicals. Vitamin E may be in the form of alpha tocopherol acetate, which is readily bioconverted to free vitamin E in the skin (Drug & Cosmetic Industry: 161: 52-56, 1997). Being an antioxidant, Vitamin E helps block lipid peroxidation and prevents the oxidation of fatty acids and lipids, key components of cellular membranes. Thus, vitamin E provides protection to the skin against peroxide radicals, stabilizes the cell membranes, and promotes normal skin cell functions.

An important property of vitamin E is that it protects against UV damage. It is well known that the UV light induces the production of free radicals in the skin. Exposure to UV light sharply reduces the level of vitamin E in the skin (Drug & Cosmetic Industry: 161: 52-56, 1977). Therefore, addition of vitamin E in composition of the present invention will aid in restoring the vitamin E levels in the skin and protect from the damaging effect of UV radiation (sun exposure).

An additional importance of vitamin E is the fact that the number of melanocytes, the melanin producing cells in the skin, in the elderly is sharply reduced, resulting in reduced melanin production (Drug & Cosmetic Industry: 161: 52-56, 1997). Since the function of melanin is to protect from the damaging effect of UV radiation, application of vitamin E is believed to provide protection to the skin of the elderly in whom melanin production has declined. Additionally, vitamin E is believed to provide enhanced protection of skin against environmental stress, such as from ozone. Furthermore, vitamin E, being a natural moisturizer, will increase skin hydration, relieve dry skin, and improve skin's smoothness and softness. Vitamin E also enhances the immune system by suppressing prostaglandins, cellular components of the immune system which are sensitive to oxidation.

Vitamin E being a natural antioxidant will prevent or delay rancidity of not only of skin lipids, but also of fatty acids and oils and their derivatives commonly present in numerous skin care products. Through this action, vitamin E should aid in extending the shelf-life of the topical formulation of the composition of the present invention.

Because the topical composition contains free amino acids, the possible presence of nitrite as a potential contaminant in other cosmetic raw ingredients may result in the formation of nitrosamines, which can be toxic to the skin. Presence of vitamin E in the present formulation will aid as a blocking agent or prevent the formation of nitrosamines in the finished product.

The topical composition may optionally include vitamin A or its derivatives such as retinal and retinoic acid. Vitamin A and its derivatives can be present in an amount within the range of 5,000 I.U. (5,000 International Units) to 10,000 I.U./g. However, other amounts are also contemplated. Vitamin A is necessary for normal growth and development and plays a major role in the differentiation of the epidermal cells. Vitamin A deficiency causes atrophy of the epithelial cells, proliferation of basal cells, and increased growth and differentiation of new cells into horny epithelium. This results in symptoms of dryness and scaliness of the skin, and excessive keratinization. Therefore, vitamin A normalizes dry and photodamaged skin and reduces scaliness. Additionally, vitamin A may improve skin's elasticity and skin thickness. Because damaged epithelial cells are susceptible to an increased infection, Vitamin A acts as an "anti-infection" agent due to its ability to repair cells and stimulate normal cell growth. Additionally, Vitamin A analogs have been shown to retard the aging process of the skin. Studies have shown that topical use of retinoic acid reverses photoaging.

The composition may optionally include vitamin $B_1$ (thiamin), a vitamin of the B-complex group. Thiamin is converted into thiamin pyrophosphate (also known as thiamin diphosphate), the coenzyme form of this vitamin. In this form, it serves as a cofactor for a number of enzymes, including the branched-chain keto acid dehydrogenase. Thus, inclusion of thiamin in the present formulation, will aid in speeding up the metabolism of branched-chain amino acids, and thus will accelerate skin lipid production. Another advantage of thiamin in the present composition is that its coenzyme, thiamin diphosphate, is an inhibitor of the branched chain keto acid dehydrogenase kinase described above. Through this inhibition, thiamin will aid in the activation of branched chain keto acid dehydrogenese, which then will speed up the metabolism of BCAAs and accelerate skin lipid production.

The composition also optionally include vitamin $B_3$ in the form of niacin or niacinamide. This vitamin is the precursor of nicotinamide adenine dinucleotide (NAD) and nicotinamide adenine dinucleotide phosphate (NADP), cofactors for branched-chain keto acid dehydrogenase and other enzymes involved in fatty acid metabolism. Additionally, niacin and its coenzymes play roles in several energy producing reactions in the skin cells and directly and indirectly aid in lipid production.

The composition may optionally include vitamin C (ascorbic acid), an important antioxidant vitamin. The skin levels of vitamin C decline due to aging, smoking, and drug intake. Consequently, skin's ability to detoxify certain toxic chemicals diminishes, resulting in damaged and unhealthy skin. The presence of vitamin C can protect from such damaging effects. By far the most important function of vitamin C is that it is essential for the synthesis of skin collagen.

If present, the total amount of panthenol in the composition generally ranges from 0.001% to 20 wt %, preferably from 0.01% to 10 wt %, and most preferably from 0.1% to 5 wt %.

If present, the total amount of pyridoxine in the composition generally ranges from 0.001% to 10 wt %, preferably from 0.01% to 5 wt %, and most preferably from 0.1% to 2 wt %.

If present, the total amount of biotin in the composition generally ranges from 0.001% to 3 wt %, preferably from 0.01% to 1.5 wt %, and most preferably from 0.05% to 0.5 wt %.

If present, the total amount of vitamin E in the composition ranges from 0.001% to 25 wt %, preferably from 0.01% to 15 wt %, and most preferably from 0.1% to 10 wt %.

If present, the total amount of each of the other vitamins is present in an amount of from 0.001 to 10 wt %, preferably 0.01 to 5 wt %, and most preferably from 0.05 to 2.0 wt %.

The topical composition may optionally include a thiol compound. An example of a useful thiol compound is DL-lipoic acid (also known as DL-6,8-thioctic acid) or salts thereof. Lipoic acid is a cofactor for branched-chain keto acid dehydrogenase. Thus, the presence of this thiol compound should aid in normal branched-chain keto acid dehydrogenase activity necessary for branched-chain amino acid metabolism and lipid production. Additionally, a derivative of lipoic acid, known as alpha-lipoic acid has been shown to be a powerful anti-oxidant in the skin. Accordingly, this may also be included in the composition of the present invention.

The composition optionally can include L-carnitine. It is well known that L-carnitine plays an important role in the oxidation of long-chained fatty acids. Research has shown that this compound also increases the oxidation of branched-chain amino acids (Paul: Am. J. Physiol. 234: E494-E499, 1978). Therefore, the presence of this compound in the present formulation will aid in the oxidation of branched-chain amino acids and thus increase the supply of small fragments to be utilized for skin lipid synthesis. Carnitine readily forms esters with CoA compounds, especially those derived from the branched-chain amino acids. Thus, the presence of carnitine is believed to accelerate the metabolism of branched-chain amino acids in a way that is beneficial for skin lipid production. The carnitine can also be provided by several derivatives of carnitine such as acetylcarnitine; propionylcarnitine; hexanoylcarnitine; octanoylcarnitine; and palmitoylcarnitine. The use of octanoylcarnitine has the added advantage of also providing octanoate. If present, the amount of L-carnitine in the composition can range from 0.001% to 20%, preferably from 0.1% to 10%, and most preferably from 0.1% to 5% by weight of the composition. Additionally, L-carnitine being a strong hygroscopic agent, may improve skin moisturization.

The composition may optionally include minerals such as magnesium, and manganese, and mixtures thereof. Both magnesium and manganese ions are activators of beta hydroxy beta methylglutaryl-CoA reductase, the rate-limiting enzyme for cholesterol synthesis (Hoppe-Seyler Z. Physiol. Chem. 363: 1217-1224, 1982). Additionally, magnesium ions convert the branched-chain keto acid dehydrogenase from its inactive form into its active form (Paul, J. Biol. Chem. 267: 11208-11214, 1992). Magnesium ions also serve as a cofactor for beta-methyl crotonyl-CoA carboxylase, which is an enzyme in leucine catabolic pathway. Manganese ions are activators of acetyl-CoA carboxylase, the rate-limiting enzyme for fatty acid synthesis (Thampy & Wakil, J. Biol. Chem. 260: 6318-6323, 1985). Therefore, by including magnesium and/or manganese ions in the composition of the present invention, lipid synthesis in the skin can be increased.

The composition also may include certain oils, such as plant oils, which can impart a desirable "touch and feel" to the topical composition. Non-limiting examples of such oils include: Evening Primrose (*Oenothera biennis*) Oil, Babassu (*Orbignya oleifera*) Oil, Avocado (*Persea gratissima*) Oil, Safflower (*Carthamus tinctorius*) Oil, Olive (*Olea europaea*) Oil, or mixtures thereof.

The composition also may comprise: an emollient, such as dimethicone and PPG-2 myristyl ether proprionate; an emulsifier, such as glyceryl stearate and PEG (polyethylene glycol); a chelating agent, such as EDTA (ethylenediaminetetraacetate); a humectant, such as glycerine; and a preservative, such as 2 phenoxyethanol or sodium hydroxymethylglycinate. A large variety of useful emollients, emulsifiers, chelating agents, humectants and preservatives are known and/or available.

Although many of the ingredients, being small molecules (e.g., less than 500 Daltons in molecular weight), readily penetrate into the epidermis, their transdermal transport could be optionally further enhanced by including the following into the composition:

Short-chained alcohols, such as ethanol or iso-propanol (Biochim. Biophys. Acta 1195: 169-179, 1994); and Alpha hydroxy acids, such as 2% glycolic acid.

According to one non-limiting embodiment, the topical composition can further comprise one or more topically-effective steroids (a "topical steroid"). A "topical steroid" is a compound that is effective for use in treatment of a dermatological condition, such as eczema, atopic dermatitis, etc., and reduces one or more symptoms of a dermatological condition, such as erythema, pruritus, exudation, excoriation, and lichenification.

Topical steroids can be classified by their relative strengths into for example low, medium, and high strength.

Examples of low strength steroids include hydrocortisone 0.5-2.5% (Hytone cream, lotion, ointment; Cortaid, Synacort, and many over-the-counter brands).

Examples of medium strength steroids include Triamcinalone acetonide 0.1-0.5%

(Kenalog, Aristocort cream); Betamethasone diproprionate 0.05% (Diprosone).

Examples of high strength steroids include Fluocinonide 0.05% (Lidex); Triamcinalone acetonide 0.5% (Kenalog cream); Mometasone furoate 0.1% (Elocon ointment); Betamethasone diproprionate 0.25% (Diprolene).

The strength of a topical steroid may be a function of the overall specific activity of the steroid, typically in comparison to hydrocortisone, and the concentration of the steroid in the drug product.)

In the context of the present compositions and methods, in certain cases it may be preferable to administer a topical steroid for the duration of treatment with the compositions described herein, or the steroid may only be administered during initial stages of treatment (1-5 days), followed by topical steroid-free compositions as described herein.

If the steroid is to be administered at the same time as the steroid-free compositions, a single drug product comprising the steroidal and non-steroidal ingredients may be employed. If the steroid is only to be administered during a first stage (or any stage) of treatment with the non-steroidal ingredients, then a composition comprising the steroid may be physically separate, and packaged separately from a steroid-free composition. The steroid-containing composition may be essentially identical to the steroid-free composition except for the presence of the steroid compound, thus simplifying administration during phases where steroid use is desired or indicated. Where the steroid is administered in a time frame that is different from the non-steroidal ingredients, the steroid may be administered during the first 1, 2, 3, 4, 5, 6, 7, 8, 9 or 10 days of treatment, or longer.)

In another embodiment of the methods or kits described herein, an anti-inflammatory, such as prednisone, may be administered orally or parenterally during stages of treatment with the topical compositions (steroid free, or containing steroid) described herein. Prednisone (typically available from 1 mg/dose to 50 mg/dose) often is taken for limited time periods to treat inflammatory conditions. Patients are typically weaned from prednisone after initial treatment of 3-14 days. Prednisone dosage regimens are well-known in the medical arts.)

The topical steroid may be administered as part of a topical composition, such as those described herein, or administered along with a composition described herein. In one embodiment, a steroid-containing composition is provided which comprises: a) L-leucine; L-isoleucine; L-valine and/or derivatives, metabolites or analogs of L-leucine, L-isoleucine, and L-valine; and mixtures thereof; and pharmaceutically acceptable salts thereof; b) one or more enzyme activators selected from the group of caprylic acid, hexanoic acid, alpha keto isocaproic acid, alpha chloroisocaproic acid, thiamin diphosphate, and derivatives or analogs thereof; and pharmaceutically acceptable salts thereof; and c) a topical steroid. One or more vitamins (such as Vitamin E) or other constituents, such as a dimethicone, as described herein, also may be included in the composition The topical steroid may also be packaged in a kit along with a topical steroid-free composition as described herein, such as a topical steroid-free composition comprising: a) L-leucine; L-isoleucine; L-valine; and/or derivatives of L-leucine, L-isoleucine, and L-valine; and mixtures thereof; and pharmaceutically acceptable salts thereof; and b) one or more enzyme activators selected from the group of caprylic acid, hexanoic acid, alpha keto isocaproic acid, alpha chloroisocaproic acid, thiamin diphosphate, and derivatives or analogs thereof; and pharmaceutically acceptable salts thereof. One or more vitamins (such as Vitamin E) or other constituents, such as a dimethicone, as described herein, also may be included in the composition. In the kit, the topical steroid is packaged in a container separate from the first composition.

By "kit," it is meant a commercial embodiment of a product that comprises as a minimum a composition as described herein contained within packaging. By "packaged", "packaging" and like terms or phrases, it is meant any useful, commercially-acceptable (and typically regulatorily acceptable) means for distribution of the compositions described herein, including containers, vials, tubes, sprayers (pump, aerosol, etc.), bubble-packs, foil-packs, blister packs, foil and/or plastic pouches, plastic containers. The packaging can be vacuum-sealed, and is preferably packaged in a sterile condition. As can be appreciated by those in the formulary arts, the choice of dosage form and typical ingredients are typically a matter of design choice and optimization, depending on the route of administration, the desired pharmacokinetics and pharmacodynamics, etc. In one embodiment, the compositions are distributed in plastic and/or foil tubes, as is the case with many dermatological compositions. The tube or other container for distributing and dispensing the composition may be packaged in a box for commercial distribution along with a label or package insert that comprises indicia indicating one or more of the ingredients, indications (for what purpose the composition may be used for, such as for treatment of one or more dermatological conditions as described herein), and directions for use of the composition. For example and without limitation, the directions may be in written form and recites the amount of the topical composition to be topically applied and the frequency of topical application. The kit can also include an applicator to aid in the topical administration of the topical composition. The applicator may be a woven and/or non-woven pad, a Q-TIP or like device, etc.

In one embodiment, a topical steroid-free composition is packaged in a first container, such as a tube, and a topical steroid-containing composition is packaged in a second container, such as a tube, and the containers are packaged together as a kit in a box, or other commercially acceptable packaging, optionally along with a package insert. In one embodiment, in which the composition comprises a topical steroid and/or a topical steroid is packaged in a kit along with the composition, and in methods of treatment of one or more symptom of a dermatological condition, as described herein, the topical steroid is provided in a low-dose.

A "topical composition" can be a lotion, salve, ointment, emulsion, cream, gel, spray, solution, etc. A topical composition can comprise one or more pharmaceutically, veterenarily or cosmetically acceptable carriers. A "carrier" includes as a class any compound or composition useful in facilitating storage, stability, administration, cell targeting and/or delivery of the topical composition, including, without limitation, suitable vehicles, skin conditioning agents, skin protectants, diluents, emollients, solvents, excipients, pH modifiers, salts, colorants, rheology modifiers, thickeners, lubricants, humectants, antifoaming agents, erodeable polymers, hydrogels, surfactants, emulsifiers, emulsion stabilizers, adjuvants, surfactants, preservatives, chelating agents, fatty acids, mono-di- and tri-glycerides and derivates thereof, waxes, oils and water. Examples of carriers include: natural oils, such as avocado oil, olive oil, and safflower oil; polydimethylsiloxane, such as dimethicone 350 and cyclomethicone.

Various types of other ingredients may also optionally be present in the topical composition, including, without limitation: sunscreens, tanning agents, skin conditioning and moisturizing agents, anti-dandruff agents, hair conditioners and hair growth stimulants.

Sunscreens include those materials commonly employed to block ultraviolet light. Illustrative compounds are the derivatives of PABA, cinnamate, and salicylate. For example, octyl methoxycinnamate and 2-hydroxy-4-methoxy benzophenone (also known as oxybenzone) can be used. Octyl methoxycinnamate and 2-hydroxy-4-methyl benzophenone are commercially available under the trademarks, Parsol MCX and Benzophenone-3, respectively. The exact amount of sunscreen employed in the emulsion can vary depending upon the degree of protection desired from the sun's UV radiation.

Another optional ingredient includes essential fatty acids (EFAs), that is, fatty acids which are essential for the plasma membrane formation of all cells. In keratinocytes, EFA deficiency causes cells to become hyperproliferative. Supplementation of EFA corrects this. EFAs also enhance lipid production of epidermis and provide lipids for the barrier formation of the epidermis. These essential fatty acids are preferably chosen from linoleic acid, gamma-linoleic acid, homo-gamma-linoleic acid, columbinic acid, arachidonic acid, gamma-linolenic acid, timnodonic acid, hexanoic acid and mixtures thereof.

The compositions may also include a hydroxy acid. Hydroxy acids enhance proliferation and increase ceramide production in keratinocytes, increase epidermal thickness, and increase desquamation of normal skin resulting in smoother, younger looking skin. Additionally, the exfoliating properties of these acids will facilitate the entry of the active compounds into the skin and, by improving the barrier, will mitigate the deleterious effects of the hydroxy acids. The hydroxy acid can be chosen from alpha-hydroxy acids, beta-hydroxy acids, other hydroxycarboxylic acids (e.g., dihydroxycarboxylic acid, hydroxydicarboxylic acid, hydroxytricarboxylic acid) and mixtures thereof or combination of their stereoisomer (D, L, or DL). See, for example, U.S. Pat. No. 5,561,158 to Yu and Van Scott, which disclose useful alpha-hydroxy acids. The hydroxy acid may be an alpha-hydroxy acid. The hydroxy acid may be is chosen from one of 2-hydroxyoctanoic acid, hydroxylauric acid, lactic acid, and glycolic acid, and mixtures thereof. The amount of the hydroxy acid component present in the composition may range from 0.01 to 20%, from 0.05 to 10% and from 0.1 to 3% by weight.

Surfactants, which are also sometimes designated as emulsifiers, may also be incorporated into the topical composition. Surfactants can comprise anywhere from about 0.5% to about 30% wt, preferably from about 1% to about 15% wt of the total composition. Surfactants may be cationic, nonionic, anionic, or amphoteric in nature and combinations thereof may be employed. Non-limiting examples of nonionic surfactants are alkoxylated compounds based upon fatty alcohols, fatty acids and sorbitan. These materials are available, for instance, from the Shell Chemical Company under the "Neodoll" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention. Non-limiting examples of anionic-type surfactants may include fatty acid soaps, sodium lauryl sulfate, sodium lauryl ether sulfate, alkyl benzene sulphonate, mono and/or dialkyl phosphates and sodium fatty acyl isothionate. Amphoteric surfactants include such material as dialkylamine oxide and various types of betaines (such as cocoamido propyl betaine).

Emollients can also be incorporated into the topical composition. Levels of such emollients may range from about 0.5% to about 50% wt, preferably between about 5% and 30% wt of the total composition. Emollients may be classified under such general chemical categories as esters, fatty acids, and alcohols, polyols and hydrocarbons. Esters may be mono- or di-esters. Non-limiting examples of fatty di-esters include dibutyl adipate, diethyl sebacate, diisopropyl dimerate, and dioctyl succinate; examples of branched-chain fatty esters include 2-ethyl-hexyl myristate, isopropyl stearate and isostearyl palmitate; examples of tri-basic acid esters include triisopropyl trilinoleate and trilauryl citrate; and examples of straight-chain fatty esters include lauryl palmitate, myristyl lactate, oleyl eurcate and stearyl oleate. For example and without limitation, esters that are emollients include coco-caprylate/caproate (a blend of coco-caprylate and coco-caproate), propylene glycol myristyl ether acetate, diisopropyl adipate and cetyl octanoate. In another non-limiting example, fatty alcohols and acids that are emollients include those compounds having from 10 to 20 carbon atoms, such as cetyl, myristyl, palmitate and stearyl alcohols and acids. In yet another non-limiting examples, polyols which may serve as emollients include linear and branched-chain alkyl polyhydroxyl compounds, such as propylene glycol, sorbitol, glycerin; polymeric polyols such as polypropylene glycol and polyethylene glycol; and penetration enhancers, such as butylene and propylene glycol. Non-limiting exemplary hydrocarbons which may serve as emollients are those having hydrocarbon chains anywhere from 12 to 30 carbon atoms, such as mineral oils, petroleum jelly, squalene and isoparaffins.

Thickeners can also be incorporated into the topical composition. For example and without limitation, a thickener is present in amounts anywhere from 0.1% to 20% by weight, preferably from about 0.5% to 10% by weight of the topical composition. Non-limiting exemplary thickeners are cross-linked polyacrylate materials available under the trademark CARBOPOL from the B. F. Goodrich Company; gums, such as xanthan, carrageenan, gelatin, karaya, pectin and locust bean gum; and other materials that may also serving as a silicone or emollient. For example and without limitation, silicone gums in excess of centistokes and esters such as glycerol stearate have dual functionality.

Many topical compositions, especially those containing water must be protected against the growth of potentially harmful microorganisms. Preservatives are, therefore, desirable. Non-limiting examples of preservatives include alkyl ester of p-hydroxybenzoic acid, hydantoin derivatives, sodium hydroxymethyl glycinate, propionate salts, a variety of quaternary ammonium compounds, methyl paraben, propyl paraben, imidazolidinyl urea, sodium dehydroxyacetate, phenoxy ethanol, and benzyl alcohol. In one non-limiting example, preservatives are present in the topical composition in amounts ranging from about 0.05% to 2% by weight of the composition.

Other adjunct components may also be incorporated into the topical composition. For example and without limitation, powders may also be incorporated into the topical composition, such as chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof. The topical composition can further comprise coloring agents, opacifiers and perfumes. For example and without limitation, amounts of these materials may range anywhere from 0.001% up to 20% by weight of the composition.

Non-limiting examples of compositions useful in the methods described herein are presented in Table 1. In Table 1, the "Range" and "Example" are provided with respect to the exemplary compound indicated in parentheses under "Ingredient." For example, for vitamin E, the Range and Example concentrations are provided for tocopherol acetate, though equivalent amounts of equivalent ingredients may be used, as are available in the compounding, pharmaceutical and cosmetic arts.

TABLE 1

Non-limiting example of useful topical composition

| Ingredient | Range (% wt.) |
| --- | --- |
| Deionized water | QS |
| Biotin (e.g., d-biotin) | 0.01-0.25% |
| Vitamin E (e.g., tocopherol acetate) | 0.10-2.50% |
| Serine (e.g., L-serine) | 0.015-0.35% |
| Vitamin B6 (e.g., pyroxidine HCl) | 0.10-2.50% |
| Panthenol (e.g., dex-panthenol) | 0.10-2.50% |
| Mono-, di-, tri- glyceryl caprylate | 0.25-5.00% |
| L-valine | 0.025-0.65% |
| L-isoleucine | 0.0075-0.20% |
| L-leucine | 0.015-0.35% |
| Glycerin | 0.50-15.0% |
| Polyoxypropylene-2 myristyl ether propionate (e.g., CRODAMOL PMP) | 0.50-15.0% |
| Glyceryl stearate/PEG 100 stearate (e.g., Arlacel-165) | 1.00-20.0% |
| Cetyl alcohol/stearyl alcohol (e.g., Cetearyl alcohol) | 1.00-20.0% |
| Cyclomethicone (e.g., Dow Corning 344 fluid) | 0.25-7.50% |
| Polydimethylsiloxane (e.g., Dimethicone 350) | 0.25-5.00% |
| Stearic acid (e.g., Hystrene-5016) | 0.25-6.50% |
| Evening primrose (*Oenothera Biennis*) oil | 0.05-1.25% |
| Babassu (*Orbignya oleifera*) Oil | 0.05-1.25% |
| Avocado (*Persea gratissima*) Oil | 0.05-1.25% |
| Safflower (*Carthamus tinctorius*) Oil | 0.05-1.25% |
| Olive (*Olea europaea*) oil | 0.05-1.25% |
| 2-phenoxyethanol | 0.05-1.25% |
| Sodium hydroxymethylglycinate (e.g., Suttoside A) | 0.10-2.50% |
| Disodium EDTA | 0.01-0.25% |

It should be noted that certain ingredients, such as the plant oils (e.g., 0.25-6.25% wt.), may be substituted with equal efficacy with other natural, mineral or synthetic oils. The same is true for other ingredients, which a person of ordinary skill in the compounding and formulary arts can substitute with equivalent results.

EXAMPLE 1

Topical Composition

A topical composition was prepared, including: Deionized Water QS % wt.; Biotin 0.050% wt.; Vitamin E 0.500% wt.; Serine 0.066% wt.; Vitamin B6 0.500% wt.; Panthenol 0.500% wt.; Glyceryl Caprylate 1.000% wt.; Valine 0.134% wt.; Isoleucine 0.039% wt.; 0.070% wt.; Glycerin 3.000% wt.; PPG-2 Myristyl Ether Propionate 3.000% wt.; Glyceryl Stearate/PEG 100-Stearate 4.500% wt.; Cetyl Alcohol/Stearyl Alcohol 4.000% wt.; Cyclomethicone 1.500% wt.; Polydimethylsiloxane 1.000% wt.; Stearic Acid 1.250% wt.; Evening Primrose (*Oenothera Biennis*) Oil 0.250% wt.; Babassu (*Orbignya Oleifera*) Oil 0.250% wt.; Avocado (*Persea Gratissima*) Oil 0.250% wt.; Safflower (*Carthamus Tinctorius*) Oil 0.250% wt.; Olive (*Olea Europaea*) Oil 0.250% wt.; 2 Phenoxyethanol 0.250% wt.; Sodium hydroxymethylglycinate 0.500% wt.; and Disodium EDTA 0.050% wt.

As it contains preservatives, this composition has passed the FDA standards in a microbial challenge. In addition, the composition has been shown to be safe for use in patients with atopic dermatitis. Formulation resulted in a white, opaque cream.

It should be noted that the mono-glyceryl caprylate is aesthetically far superior to using caprylic acid as an enzyme activator because it has been found that caprylic acid, in many cases was unacceptable due to its odor.

EXAMPLE 2

Methods and Protocols for Clinical Usage and Regression Study for Atopic Dermatitis Using the Composition of Example 1

At Visit 1 (Baseline), prospective subjects completed an Eligibility and Health Questionnaire and read and signed an Informed Consent Agreement, a Confidentiality Agreement, and a Photography Release Form. Prospective subjects arrived at the clinic having refrained from drinking hot beverages within one hour and from wetting the atopic dermatitis lesions within 2 hours of the visit. Subjects with a history of active atopy for at least 3 years; at least one mild to moderate atopic lesion, covering no more than 20% of the body surface area; and clinically verified mild to moderate atopic tendencies qualified for study participation. Atopy diagnosis is based on the Rajka and Langeland criteria, presented below in Table 3.

TABLE 3

Grading (Severity) of Atopic Dermatitis

| Definition | Score |
|---|---|
| I. Extent (childhood and adult phase) | |
| Less than approximately 9% of the body area involved | 1 |
| Involvement evaluate to be more than score 1, less than score 3 | 2 |
| More than approximately 36% of the body area involved | 3 |
| II. Course | |
| More than 3 months of remission during a year | 1 |
| Less than 3 months remission during a year | 2 |
| Continuous course | 3 |
| III. Intensity | |
| Mild itch, only exceptionally disturbing night's sleep | 1 |
| Itch, evaluated to be more than score 1, less than score 3 | 2 |
| Severe itch, usually disturbing night's sleep | 3 |

Scores of 1.5 and 2.5 may also have been used on all three grading scales listed above. Clinical scores of 3 to 7.5 qualified subjects for study participation, where 3 to 4=mild, 4.5 to 7.5=moderate; and 8 to 9=severe.

Qualified subjects participated in the following clinical evaluations.

Investigator's Global Assessment (IGA): The Investigator graded the global assessment of each subject's atopic area using the following scale in Table 4.

TABLE 4

Grading of Investigator's Global Assessment (IGA)

| Score | Grade | Definition |
|---|---|---|
| 0 | Clear | No inflammatory signs of atopic dermatitis. |
| 1 | Almost Clear | Just perceptible erythema and just perceptible papulation induration. |
| 2 | Mild | Mild erythema and mild papulation induration. No oozing or crusting. |
| 3 | Moderate | Moderate erythema and moderate population induration. Oozing and crusting may be present |
| 4 | Severe | Severe erythema and severe papulation induration. Oozing and crusting is present. |

Atopic Dermatitis Severity Index (ADSI): The summary score from the 5 clinical features of atopic dermatitis—erythema, pruritus, exudation, excoriation, and lichenification—was assessed on each subject's selected target lesion using the following 4-point scales as shown in Table 5.

TABLE 5

Grading of Atopic Dermatitis Severity Index (ADSI)

| Score | Grade | Description |
|---|---|---|
| Erythema (redness present specifically In the target lesion) | | |
| 0 | None | No redness |
| 0.5 | * | |
| 1.0 | Mild | Mildly detectable erythema; pink |
| 1.5 | * | |
| 2.0 | Moderate | Dull red; clearly distinguishable |
| 2.5 | * | |
| 3.0 | Severe | Deep, dark red; marked and extensive |
| Pruritus (itching present specifically in the target lesion) | | |
| 0 | None | No itching |
| 0.5 | * | |
| 1.0 | Mild | Occasional, slight itching |
| 1.5 | * | |
| 2.0 | Moderate | Constant or intermittent itching; does not disturb sleep |
| 2.5 | * | |
| 3.0 | Severe | Bothersome itching that disturbs sleep or normal activity |
| Exudation (oozing or crusting of the target lesion) | | |
| 0 | None | No oozing or crusting |
| 0.5 | * | |
| 1.0 | Mild | Minor or faint signs of oozing |
| 1.5 | * | |
| 2.0 | Moderate | Definite oozing or crusting present |
| 2.5 | * | |
| 3.0 | Severe | Marked and extensive oozing or crusting present |
| Excoriation (evidence of scratching in the target lesion) evidence of scratching in the target lesion) | | |
| 0 | None | No evidence of excoriation |
| 0.5 | * | |
| 1.0 | Mild | Mild excoriation present |
| 1.5 | * | |
| 2.0 | Moderate | Definite excoriation present |
| 2.5 | * | |
| 3.0 | Severe | Marked, deep, or extensive excoriation present |
| Lichenification (epidermal thickening of the target lesion) | | |
| 0 | None | No epidermal thickening |
| 0.5 | * | |
| 1.0 | Mild | Minor epidermal thickening |
| 1.5 | * | |
| 2.0 | Moderate | Moderate epidermal thickening; accentuated skin lines |
| 2.5 | * | |

TABLE 5-continued

Grading of Atopic Dermatitis Severity Index (ADSI)

| Score | Grade | Description |
|---|---|---|
| 3.0 | Severe | Severe epidermal thickening; deeply accentuated skin lines |

The intermediate (half-step) grades represent mid-points between defined grades.

Prior to instrumentation, subjects rested quietly for at least 20 minutes to acclimate to ambient temperature and humidity conditions. During the course of the study, the waiting and instrumentation rooms were maintained at a temperature of 66° F. to 75° F. with a relative humidity of 13% to 22%.

Dermalab: Assessment of Trans-Epidermal Water Loss and Skin Barrier Function.

The Dermalab (manufactured by Cortex Technologies), in conjunction with a computer, measures trans-epidermal water loss (TEWL) utilizing an open chamber system. A hand-held probe placed on the skin surface samples the relative humidity at two points above the surface, allowing the rate of water loss to be calculated from the measured humidity gradient. Each TEWL measurement was taken over 60 seconds. A single Dermalab measurement was taken on the selected atopic lesion area to assess TEWL.

Corneometer: Assessment of Skin Hydration.

The Corneometer CM 825 (Courage+Khazaka, Germany) was used in conjunction with product treatment to measure product effects on the skin surface of the atopic lesion area. The Corneometer quantifies moisture content in the stratum corneum by an electrical capacitance method. The measurements have no units, but are related to the change in capacitance of the surface layers of the skin, and increase as the skin becomes more hydrated. The readings are directly related to the skin's electrical capacitance (picoFarads). Triplicate Corneometer measurements were taken on the selected atopic lesion and an adjacent non-lesional, non-tape stripped site to assess skin hydration.

Digital Photography:

One digital photograph (using a Nikon digital camera, Nikkor 60 millimeter F/2.8D lens, fitted with a Canfield TwinFlash and a polarizing filter) was taken of the atopic lesion from a selected portion of the subject population. The camera was mounted on a stationary frame so that the lens was approximately 35 centimeters from the test site. Each image required fine focusing due to the variability of the site size; however, the focal length was maintained the same for all subjects. Each photograph captured approximately 6 inches of the selected body part. Photographs taken at post-baseline visits were compared to the Baseline photo to ensure consistent focus, lighting, placement, and color. At each photography visit, color standards were photographed prior to beginning each day's photography.

Tape Stripping: A Controlled Barrier Disruption Method.

Prior to tape stripping, the test sites were cleansed with alcohol. Superficial wounds were created using clinical-selected tape on an adjacent non-lesional site. A tape-strip was placed on the wound site with approximately the same pressure and removed with a quick stroke. This was repeated for up to 50 tape-strips, or until a "glistening" layer was observed. Each tape-strip was rotated 90 degrees on the test site. The tape-stripped wound was approximately 1 inch×1 inch. Dermalab measurements were taken at Baseline prior to wounding and post wounding to verify skin barrier damage. A Dermalab measurement in the range of 4 to 6 times the Baseline score served to confirm the barrier disruption.

The skin appearance held priority over the Dermalab measurements if a site was determined to appear damaged enough to the Investigator or the Investigator's designate, even if a TEWL did not reach the targeted Dermalab value.

Subjects were distributed units of the topical composition of Example 1, a calendar of future visits, a daily diary (to record flare ups, treatment with corticosteroid, pain, itching, and quality of sleep), and the following detailed verbal and written usage and study instructions:

Usage Instructions: Apply a sufficient amount of the composition of Example 1 to the assigned areas twice per day (once in the morning and once in the evening).

At Visit 2 (Week 2), Visit 3 (Week 4), Visit 4 (Week 6), Visit 5 (3 days after Week 6), Visit 6 (7 days after Week 6), and Visit 7 (14 days after Week 6), subjects returned to the clinic. Subjects received clinical grading, Dermalab measurements, Corneometer measurements, and digital photography, in accordance with the Baseline procedures. At Visit 4, subjects received tape stripping and completed Self-Assessment Questionnaires. The daily diaries were returned and reviewed for compliance. New diaries were distributed at Visit 2, Visit 3, Visit 4, Visit 5, and Visit 6. At Visit 4, the test materials were returned to the clinic. During the regression portion of the study (between Visit 4 and Visit 7), no test materials were applied to the test sites.

Biostatistics: Mean post-baseline scores of the clinical grading, Dermalab measurements and corneometer measurements were statistically compared to mean Baseline scores for significant differences at the $P<0.05$ level using paired t-tests.

Electronic data capture (EDC) methods were used to record all clinical grading and instrumentation. Where EDC methods were captured, no paper copies were generated.

EXAMPLE 3

Single-Center Study of the Composition of Example 1 in Treating Atopic Dermatitis Summary: A single-center, clinical usage and regression study was conducted to evaluate the safety and efficacy of the topical composition of Example 1 in the management of mild to moderate atopic dermatitis. A total of 32 subjects completed the study. The study was conducted over the course of eight weeks: Week 1 through Week 6 for the usage portion and Week 6 through Week 8 for the regression portion. During the course of the usage portion of the study, subjects applied the test materials twice daily (morning and evening), as instructed. No test materials were applied during the regression portion of the study. Clinical evaluations were conducted at Visit 1 (Baseline), Visit 2 (Week 2), Visit 3 (Week 4), Visit 4 (Week 6), Visit 5 (3 days after Week 6), Visit 6 (7 days after Week 6), and Visit 7 (14 days after Week 6). Subjects participated in the following clinical evaluations at each indicated time point: Clinical Grading using the Atopic Dermatitis Severity Index (ADSI) and the Investigator's global assessment (IGA); Dermalab measurements on a selected atopic lesion area to assess trans-epidermal water loss (TEWL); triplicate Corneometer measurements were taken on the selected atopic lesion to assess skin hydration; digital photograph was taken of the atopic lesion from a selected portion of the subject population; and at Week 6, each subject completed a Self-Assessment Questionnaire to assess the efficacy of the test material. Overall, the topical composition was shown to be well tolerated and significantly effective in improving the symptoms of mild to moderate atopic dermatitis in adults.

Test product use: Individual test material units were weighed prior to distribution at Visit 1 (Baseline) and at Visit 4 (Week 6). The average amount of test product used by each study participant during the course of 6 weeks study was 177.0±9.8 g, mean±SEM, n=32.

Sixty-seven (67) subjects were screened for eligibility in the clinical study. Thirty-six (36) subjects were enrolled in the study, and the remaining thirty-one (31) subjects did not meet the inclusion criteria. Four (4) subjects were discontinued from study participation due to the following reasons: Subjects 045, 049, and 063 voluntarily withdrew; and Subject 026 had an adverse event.

Subject Demographics: Thirty-two (32) subjects completed the study. Table 6 presents each subject's gender, ethnicity, and date of birth. Ethnicity information was obtained from each subject's Eligibility and Health Questionnaire. Table 7 contains a summary of the demographic information.

TABLE 6

Subject Demographics

| Subject Number | Gender | Ethnicity | Date of Birth |
| --- | --- | --- | --- |
| 001 | Female | Caucasian | Oct. 17, 1977 |
| 002 | Female | Caucasian | Sep. 08, 1967 |
| 005 | Male | Caucasian | Aug. 06, 1982 |
| 007 | Female | Hispanic | Nov. 04, 1964 |
| 008 | Female | Caucasian | Dec. 19, 1979 |
| 011 | Female | Caucasian/Native | Oct. 17, 1977 |

TABLE 6-continued

Subject Demographics

| Subject Number | Gender | Ethnicity | Date of Birth |
| --- | --- | --- | --- |
| 012 | Female | American/Hispanic Caucasian | May 23, 1970 |
| 016 | Male | Caucasian | May 28, 1969 |
| 017 | Male | African American | May 12, 1988 |
| 018 | Female | Caucasian | Dec. 01, 1981 |
| 019 | Female | Caucasian | Dec. 13, 1978 |
| 020 | Female | Caucasian | Sep. 26, 1960 |
| 024 | Male | Caucasian | Jul. 04, 1985 |
| 025 | Male | Caucasian | May 25, 1985 |
| 027 | Male | Asian | Aug. 21, 1991 |
| 028 | Female | Caucasian | Jun. 06, 1968 |
| 030 | Female | Caucasian | Jun. 07, 1965 |
| 032 | Female | Caucasian | Feb. 20, 1971 |
| 033 | Female | Caucasian | Apr. 23, 1965 |
| 034 | Female | Caucasian | Jun. 19, 1987 |
| 041 | Male | Caucasian | Jul. 08, 1990 |
| 042 | Male | Caucasian | Aug. 15, 1985 |
| 046 | Male | Caucasian | Apr. 18, 1965 |
| 052 | Female | Caucasian | Aug. 18, 1990 |
| 053 | Female | Caucasian | Jan. 31, 1976 |
| 055 | Male | Hispanic | Dec. 16, 1990 |
| 056 | Male | Hispanic | Jan. 31, 1993 |
| 057 | Female | Caucasian | Mar. 05, 1975 |
| 060 | Female | Hispanic | Oct. 25, 1972 |
| 061 | Female | Caucasian | Oct. 30, 1988 |
| 065 | Female | Caucasian | Nov. 23, 1966 |
| 066 | Female | Caucasian | Nov. 09, 1961 |

TABLE 7

Demographic Summary

| Age (Years) | | |
| --- | --- | --- |
| Mean Age ± Standard Deviation | | 31.64 ± 10.10 |
| Minimum Age | | 16.03 |
| Maximum Age | | 48.37 |

Clinical Evaluation: The study was conducted in two phases: a treatment phase of six weeks, and a regression phase of two weeks. During the treatment phase, participants used the composition, and during the regression phase the use of the composition was discontinued but clinical grading and biophysical measurements were continued. At Visit 1 (Baseline), Visit 2 (Week 2), Visit 3 (Week 4), Visit 4 (Week 6), Visit 5 (3 days after Week 6), Visit 6 (7 days after Week 6), and Visit 7 (14 days after Week 6), subjects received clinical grading, Dermalab measurements (measures the rate of TEWL), and Corneometer measurements (a measure of skin hydration). Table 8 presents the n-values recorded per time point.

TABLE 8 n-values per time point

| | Baseline | Week 2 | Week 4 | Week 6 | 3 days after Week 6 | 7 days after Week 6 | 14 days after Week 6 |
| --- | --- | --- | --- | --- | --- | --- | --- |
| Clinical Grading | 32 | 32 | 32 | 32 | 16* | 32 | 32 |
| Dermalab | 32 | 29 | 30 | 31 | 16* | 32 | 32 |
| Corneometer | 32 | 32 | 32 | 32 | 16* | 32 | 32 |

Due to severe weather conditions, only 16 subjects were able to come to the clinic for evaluation.

Table 9 presents the results of clinical grading compared to Baseline. Mean values at each post-baseline visit were statistically compared to mean Baseline values for significant differences. The standard deviation (SD) is presented for each post-baseline time point. The use of the composition, just for two weeks, resulted in a significant decrease in clinical grades and there were further progressive decreases in clinical grades at weeks four and six. A decrease in clinical grade reflects an improvement of atopic dermatitis symptoms.

When the use of the composition was discontinued (regression phase), as to be expected, there was a gradual increase in clinical grades. An increase in clinical grades reflects reoccurrence of clinical symptoms. However, even at two weeks after discontinuing the treatment, the clinical grade values were significantly lower than the Baseline values (Table 9). The residual effects of treatment are exceptional, where the mean values for ADSI are lower than pre-treatment levels even after 14 days past Week 6.

Visual appearance: The effect of BRT-FC-83C (this product has now been trademarked under the trade name Theratopic®) was also assessed visually by taking digital photographs of the skin lesion under controlled conditions. There was a significant improvement of skin lesions during the six-weeks of the treatment phase. In many cases, the skin lesion had resolved by 6 weeks of product use. When the treatment was stopped, there was a gradual reoccurrence of the lesions (photographs not shown).

Participant's Self Assessment: At Visit 4 (Week 6), subjects completed Self-Assessment Questionnaires. Table 11 presents a tabulation of the questionnaires, which shows the number of subjects with the specific response is listed and is followed by the corresponding percentage of the total subject sample in parentheses. Nearly 85% participants said that their eczema had improved within 2 weeks of product use. Sixty one percent participants noted eczema improvement between 40-100% (Table 11).

TABLE 9

Mean Values for Clinical Grading compared to Baseline

| | Baseline | Treatment Phase | | | | | | Regression Phase | | | | |
| | | Week 2 | Week 4 | | Week 6 | | 3 Days after Week 6 | | 7 Days after Week 6 | | 14 Days after Week 6 | |
| | Mean | Mean | Mean | SD | Mean | SD | Mean | SD | Mean | SD | Mean | SD |
|---|---|---|---|---|---|---|---|---|---|---|---|---|
| Erythema | 1.73 | 1.44⇓ | 1.31⇓ | 0.44 | 1.19⇓ | 0.49 | 1.34⇓ | 0.56 | 1.38⇓ | 0.52 | 1.44⇓ | 0.46 | 0.42 |
| Excoriation | 1.34 | 0.72⇓ | 0.55⇓ | 0.58 | 0.53⇓ | 0.62 | 0.41⇓ | 0.56 | 0.61⇓ | 0.58 | 0.75⇓ | 0.62 | 0.60 |
| Exudation | 0.19 | 0.13 | 0.08⇓ | 0.25 | 0.06⇓ | 0.28 | 0.09 | 0.31 | 0.14 | 0.30 | 0.16 | 0.29 | 0.18 |
| Lichenification | 1.63 | 1.30⇓ | 1.22⇓ | 0.47 | 1.14⇓ | 0.51 | 1.22⇓ | 0.55 | 1.23⇓ | 0.49 | 1.30⇓ | 0.56 | 0.53 |
| Pruritus | 1.86 | 1.17⇓ | 0.91⇓ | 0.64 | 0.83⇓ | 0.73 | 1.13⇓ | 0.80 | 1.23⇓ | 0.66 | 1.33⇓ | 0.86 | 0.77 |
| ADSI | 6.75 | 4.75⇓ | 4.06⇓ | 1.82 | 3.75⇓ | 1.97 | 4.19⇓ | 2.10 | 4.59⇓ | 1.69 | 4.97⇓ | 2.05 | 1.86 |
| Global Assessment | 2.38 | 1.97⇓ | 1.67⇓ | 0.56 | 1.38⇓ | 0.73 | 1.44⇓ | 0.81 | 1.67⇓ | 0.82 | 1.89⇓ | 0.83 | 0.78 |

⇓ indicates a statistically significant (p ≤ 0.05) decrease compared to Baseline Table 10 presents the results of the clinical grading compared to Week 6. Mean values at each post-Week 6 visit (the regression portion of the study) were statistically compared to mean Week 6 values for significant differences. The standard deviation (SD) is presented for each post-baseline time point.

TABLE 10

Mean Values for Clinical Grading compared to Week 6

| | Treatment Phase Week 6 | Regression Phase | | | | |
| | | 3 Days after Week 6 | | 7 Days after Week 6 | | 14 Days after Week 6 | |
| | Mean | Mean | SD | Mean | SD | Mean | SD |
|---|---|---|---|---|---|---|---|
| Erythema | 1.19 | 1.34 | 0.31 | 1.38 ↑ | 0.40 | 1.44 ↑ | 0.36 |
| Excoriation | 0.53 | 0.41 | 0.52 | 0.61 | 0.54 | 0.75 | 0.71 |
| Exudation | 0.06 | 0.09 | 0.17 | 0.14 | 0.29 | 0.16 | 0.27 |
| Lichenification | 1.14 | 1.22 | 0.13 | 1.23 ↑ | 0.20 | 1.30 ↑ | 0.32 |
| Pruritus | 0.83 | 1.13 | 0.76 | 1.23 ↑ | 0.73 | 1.33 ↑ | 0.83 |
| ADSI | 3.75 | 4.19 | 1.38 | 4.59 ↑ | 1.40 | 4.97 ↑ | 1.86 |
| Global Assessment | 1.38 | 1.44 | 0.29 | 1.67 ↑ | 0.55 | 1.89 ↑ | 0.59 |

↑ indicates a statistically significant (p ≤ 0.05) increase compared to Baseline

TABLE 11

Results of Self-Assessment Questionnaire Analysis

| Question | Answer | n (percentage) |
|---|---|---|
| 1. If your eczema or dermatitis improved: how soon after using this cream did you see the improvement? | Within one week | 11 (42.3%) |
| | Within two weeks | 11 (42.3%) |
| | Within four weeks | 3 (11.5%) |
| | Within six weeks | 1 (3.8%) |
| 2. How much did your eczema or dermatitis improve with the new product? | Cleared totally (100%) | 4 (12.9%) |
| | 60-80% | 7 (22.5%) |
| | 40-60% | 8 (25.8%) |
| | 20-40% | 5 (16.1%) |
| | Less than 20% | 7 (22.5%) |

Skin hydration: The effect of the composition on skin hydration was measured by a corneometer. Table 12 presents the results of corneometer reading compared to baseline values. There was a significant increase in the corneometer values by week 2 of the study as compared to the baseline value. Corneometer values remained significantly higher than the baseline value at weeks 4 and 6 of the study. A higher corneometer value reflects an increase in skin hydration. When the treatment was stopped, there was a gradual decrease in the corneometer values and by two weeks of the regression period the corneometer values were similar to the baseline values.

TABLE 12

Mean Values for Corneometer and Dermalab compared to Baseline

|  | Baseline | Treatment Phase | | | | | | Regression Phase | | | | | |
|---|---|---|---|---|---|---|---|---|---|---|---|---|---|
|  |  | Week 2 | | Week 4 | | Week 6 | | 3 Days after Week 6 | | 7 Days after Week 6 | | 14 days after Week 6 | |
|  | Mean | Mean | SD | Mean | SD | Mean | SD | Mean | SD | Mean | SD | Mean | SD |
| Corneometer | 16.61 | 20.98 ⇑ | 8.24 | 21.32 ↑ | 6.63 | 21.57 ↑ | 7.34 | 18.75 | 6.18 | 18.07 | 6.13 | 16.61 | 6.13 |
| Dermalab | 34.94 | 23.26 ⇓ | 17.64 | 21.85 ↓ | 16.72 | 26.72 ↓ | 19.86 | 30.28 | 16.50 | 34.02 | 32.61 | 34.02 | 32.61 |

↑ indicates a statistically significant ($p \leq 0.05$) increase compared to Baseline;
↓ indicates a statistically significant ($p \leq 0.05$) decrease compared to Baseline Table 13 describes the results of Corneometer and Dermalab during the two-week regression phase as compared to Week 6. When the treatment was discontinued, there was a gradual decrease in the corneometer values. Corneometer values at each post-week 6 (the regression period of the study) were also compared to week 6 values for significant differences. As shown in Table 13, there was no significant difference in corneometer reading at day 3 of the regression period. However, the corneometer values at day 7 and 14 of the regression period were significantly lower than the values at week 6. These results imply that when the treatment was stopped, the skin hydration levels were well maintained for up to three days, but had decreased by day 7 and 14.

TABLE 13

Mean Values for Corneometer and Dermalab compared to Week 6

|  | Treatment Phase Week 6 | Regression Phase | | | | | |
|---|---|---|---|---|---|---|---|
|  |  | 3 Days after Week 6 | | 7 Days after Week 6 | | 14 Days after Week 6 | |
|  | Mean | Mean | SD | Mean | SD | Mean | SD |
| Corneometer | 21.57 | 18.75 | 4.35 | 18.07 ↓ | 6.48 | 16.61 ↓ | 7.16 |
| Dermalab | 26.72 | 28.09 | 9.48 | 34.50 | 30.25 | 34.50 | 30.25 |

↓ indicates a statistically significant ($p \leq 0.05$) decrease compared to Week 6

Transepidermal Water Loss (TEWL): The effect of the composition on the rate of TEWL was measured by a Dermalab, without disrupting the skin barrier. As shown in Table 12, use of the composition significantly decreased the rate of TEWL within two weeks. The rate of TEWL remained significantly lower than the baseline at weeks 4 and 6 of the treatment phase. A lower rate of TEWL is consistent with an improvement of the barrier function of the skin, and typically has an inverse relationship to the skin hydration level. During the two-week regression phase of the study, the TEWL values gradually increased, and by two-week the values were similar to the Baseline value (Table 12). When the treatment was discontinued, there was a gradual increase in the Dermalab values (as shown in Table 13).

At Visit 1 (Baseline) and Visit 4 (Week 6), subjects received tape stripping. Dermalab measurements were taken at Baseline prior to wounding and post wounding to verify skin barrier damage. Table 14 presents the results of the mean values and the difference between the pre- and post-tape stripping.

Skin Barrier Function: Skin barrier function was then determined by measuring the rate of TEWL by Dermalab at baseline and after six-week use of the composition. At both time points, TEWL was determined before and after disruption of the skin barrier by tape-stripping. A measure of the barrier function was determined from the difference in TEWL between pre- and post-stripping of the barrier. As shown in Table 14, the difference in TEWL between pre- and post-stripping was significantly lower at week 6 of product use as compared to the baseline. A lower rate of TEWL at week 6 is consistent with an improvement in the barrier function by the use of the investigation product.

TABLE 14

Skin Barrier Function

|  | Pre-Tape Stripping | Post-Tape Stripping | Difference between Pre- and Post-Tape Stripping | Standard Deviation |
|---|---|---|---|---|
| Baseline | 17.90 | 60.86 | 42.96 | 28.81 |
| Week 6 | 14.08 | 51.96 | 37.88* | 25.23 |

*Significantly different from Baseline at $P < 0.05$

Adverse Event: During the course of the study, one subject reported experiencing an adverse event. The following contains a brief description of the initial adverse event and resolution, dates of reaction onset and resolution, and the relationship to the test material. Subject 026 reported that the atopic dermatitis condition had worsened. The atopic dermatitis had spread from the original site (right palm) to both hands and wrists. Subject was observed to have moderate erythema, no exudation, minimal excoriation, and moderate to severe lichenification. Subject normally applied Fluocinonide, 0.05% (60 g) ointment to treat his eczema. Therefore, subject applied Fluocinonide, 0.05% (60 g) ointment to treat the atopic dermatitis. Eczematous plaque was observed on both palms and fingertips of hands. The subject described moderate pain when bending his fingers and found working to be difficult. The subject is a contract worker and has been working with drywall and mudding for the last week or so. This type of work condition normally causes his eczema to flare. The subject tried to use vinyl gloves to protect his hands, but they rip easily. He was unable to use other gloves due to their cumbersome quality and the fact that they stay wet while mudding. Because of subject's work environment, below, the Adverse Event's Relationship to the composition was classified as "Possibly Related". The test material was discontinued, and Subject received Kenalog and Lidex (fluocinonide) ointment to apply twice daily with emollients. The adverse event resolved shortly after one week.

Conclusions: This single-center, clinical usage and regression study was conducted to evaluate the safety and efficacy of the composition in the management of mild to moderate atopic dermatitis. A total of 32 subjects completed the study.

The study was conducted over the course of eight weeks: Week 1 through Week 6 for the usage portion and Week 6 through Week 8 for the regression portion. During the course of the usage portion of the study, subjects applied the test materials twice daily (morning and evening), as instructed. No test materials were applied during the regression portion of the study. Each participant served as his/her own control and the results were compared with the participant's Baseline values.

Overall, the composition of Example 1 was shown to be well tolerated and significantly effective in improving the symptoms of mild to moderate atopic dermatitis in adults. Significant clinical improvement became apparent within two weeks of using the study product (Table 9). Clinical assessment showed significant improvement in the Atopic Dermatitis Severity Index (ADSI) and the Investigator's Global Assessment (IGA) for the selected lesion at all post-baseline treatment times (2, 4 & 6 weeks). In many dermatoses, including atopic dermatitis, skin erythema is often associated with burning and stinging sensation. In the present study, the use of BRT-FC-83C resulted in significant decreases in clinical grading of erythema (Table 9), suggesting that burning and stinging sensations were also similarly decreased in the study participants.

During the regression portion of the study (discontinuation of BRT-FC-83C for 2 weeks post treatment phase), ADSI and IGA remained stable during the first 3 days of regression but became significantly higher at weeks 1 and 2 of regression, suggesting that the improvement obtained in atopic dermatitis severity during the treatment phase remained stable for the first 3 days of non-treatment. Although ADSI and IGA increased at weeks 1 and 2 of regression, these values were still significantly lower than the Baseline values. These results suggest that the disease severity remained suppressed for 2 weeks, and possibly longer, after the treatment was stopped. By implication, if a person were to skip the use of the product for few days, the atopic dermatitis symptoms are likely to remain under control. In addition to the clinical grading, improvement was also demonstrated by visual appearance of the skin as documented by photography of target atopic lesions.

Results of the Self-Assessment Questionnaire showed that a significantly greater proportion of the subject population responded positively than negatively to the benefits of the product.

Besides the clinical improvement, the product was also found to improve the biophysical parameters. For example, target lesion Corneometer measurements of skin hydration significantly improved after baseline for all treatment visits, but returned to baseline range at all regression time-points. Similarly, Transepidermal Water Loss (TEWL), an indicator of barrier function, improved at all treatment visits, but returned to baseline range during weeks 1 and 2 of regression. To further evaluate skin barrier function, tape-stripping was used to disrupt the barrier by essentially removing the stratum corneum in the tape-stripped location. The number of tape-strips necessary to reach the glistening layer is related to the health of the skin barrier. The results of pre- and post-tape stripping at a site adjacent to lesional skin at baseline and week 6 suggests that the skin barrier function was significantly enhanced during the 6 weeks of treatment. BRT-FC-83C was shown to improve the signs and symptoms of atopic dermatitis, and its ability to improve the skin barrier function and facilitate healing, suggests that in addition to being beneficial for the treatment of mild to moderate atopic dermatitis, the product may also be of benefit for other skin conditions where the barrier is compromised, such as psoriasis, seborrheic dermatitis, radiation dermatitis, irritant contact dermatitis, and other similar dermatoses.

Currently, the mainstay of atopic dermatitis treatment is the use of topical corticosteroid creams to reduce inflammation. However, the long-term use of topical corticosteroids is contraindicated, especially around the face due to potential side effects. Based on the results of this study, the composition, which does not contain corticosteroids, provides a safe and effective alternative to corticosteroids for the management of the clinical signs and symptoms of mild to moderate atopic dermatitis.

Having described this invention, it will be understood to those of ordinary skill in the art that the same can be performed within a wide and equivalent range of conditions, formulations and other parameters without affecting the scope of the invention or any embodiment thereof.

The invention claimed is:

1. A method of treating a person of any age with an inflammatory dermatological condition having one or more of the symptoms of erythema, pruritus, exudation, excoriation, and lichenification comprising:
    (a) providing a topical composition having:
        (i) one or more components selected from the group of L-leucine, L-isoleucine, L-valine, derivatives, metabolites or analogs of L-leucine, L-isoleucine, L-valine and a mixture thereof;
        (ii) about 1.0% mono-, di-, or tri-glyceryl caprylate; and
        (iii) polydimethylsiloxane;
    (b) topically administering an effective amount of the topical composition to the person's skin to treat the inflammatory dermatological condition and relieve the symptoms.

2. The method as recited in claim 1 wherein the topical composition is administered for at least six weeks.

3. The method of claim 1 wherein treatment is stopped after six weeks and wherein the symptoms are suppressed for at least one day.

4. The method of claim 2 wherein treatment is stopped after six weeks and wherein the symptoms remain suppressed for about one to 14 days.

5. The method of claim 1 wherein the topical composition is administered from one day to a year.

6. The method of claim 1 wherein the method further comprises topically administering a topical steroid for a period from one to seven days before topically administering the topical composition.

7. The method of claim 1, wherein the method further comprises topically administering a topical steroid to the person prior to or concurrently with administering the topical composition.

8. The method of claim 1, wherein the derivative, metabolite or analog of L-leucine, L-isoleucine, and L-valine is selected from the group consisting of: nitrogen-free analogues of L-leucine, L-isoleucine and L-valine; branched chain keto acids derived from L-leucine, L-isoleucine, and L-valine; isovaleryl-CoA; isovalerylcarnitine; isovalerylglycine; isovaleric acid; beta-methylcrotonyl-CoA, beta-methylcrotonylcarnitine; beta-methylcrotonylglycine; beta-methylcrotonic acid; beta-methylglutaconyl-CoA; beta-methylglutaconylcarnitine; beta-methylglutaconylglycin; beta-methylglutaconie acid; beta-hydroxy-beta-methylglutaryl-CoA; beta-hydroxy-beta-methylglutarylcarnitine; beta-hydroxy-beta-methylglutarylglycine; beta-hydroxy-beta-methylglutaric acid; acetyl-CoA; acetylcarnitine; acetylglycine; acetoacetyl-CoA; acetoacetylcarnitine; acetoacetylglycine; isobutyryl-CoA; isobutyrylcarnitine; isobutyrylglycine; isobutyric acid; methylacrylyl-CoA;

methylacrylylcarnitine; methylacrylylglycine; methylacrylic acid; beta-hydroxyisobutyryl-CoA; beta-hydroxyisobutyrylcarnitine; beta-hydroxyisobutyrylglycine; beta-hydroxyisobutyric acid; methylmalonate semialdehyde; propionyl-CoA; propionylcarnitine; propionylglycine; propionic acid; D, L, or DL-methylmalonyl-CoA; D, L, or DL-methylmalonylcarnitine; D, L, or DL-methylmalonylglycine; methylmalonic acid; succinyl-CoA; succinylcarnitine; succinylglycine; succinic acid; alpha-methylbutyryl-CoA; alpha-methylbutyrylcarnitine; alpha-methylbutyrylglycine; alpha-methylbutyric acid; tiglyl-CoA; tiglylcarnitine; tiglylglycine; tiglic acid; alpha-methyl-beta-hydroxybutyryl-CoA; alpha-methyl-beta-hydroxybutyrylcarnitine; alpha-methyl-beta-hydroxybutyryiglycine; alpha-methyl-beta-hydroxybutyric acid; alpha-methylacetoacetyl-CoA; alpha-methylacetoacetylcarnitine; alpha-methylacetoacetylglycine; alpha-methylacetoacetic acid; and mixtures thereof.

9. The method of claim 1 wherein the method further comprises administering prednisone orally or parentally during the stages of treatment with the topical composition.

10. The method of claim 1, wherein one or more components are selected from the group consisting of L-leucine; L-isoleucine; and L-valine.

11. The method of claim 1, wherein the topical composition further comprises one or more vitamins selected from the group consisting of: panthenol, pyridoxine, biotin, and vitamin E.

12. The method of claim 11, wherein the topical composition comprises between 0.025% and 0.65% of L-valine; between 0.0075% and 0.20% of L-isoleucine; between 0.015% and 0.35% of L-leucine; and between 0.01% and 2.5% of one or more vitamins.

13. The method of claim 1, wherein the topical composition comprises: deionized water, biotin, vitamin E, serine, vitamin B6, panthenol, L-valine, L-isoleucine, L-leucine, glycerin, polyoxypropylene-2 myristyl ether propionate, glyceryl stearate/PEG 100 stearate, cetyl alcohol/stearyl alcohol, cyclomethicone, stearic acid, one or more plant oils, 2-phenoxyethanol, sodium hydroxymethylglycinate, and disodium EDTA.

14. The method of claim 1, wherein the topical composition further comprises one or more plant oils selected from the group consisting of evening primrose (*Oenothera Biennis*) oil, babassu (*Orbignya oleifera*) oil, avocado (*Persea gratissima*) oil, safflower (*Carthamus tinctorius*) oil, and olive (*Olea europaea*) oil.

15. The method of claim 1, wherein the composition consists essentially of deionized water, QS; biotin, 0.01-0.25%; vitamin E, 0.10-2.50%; serine, 0.015-0.35%; vitamin B6, 0.10-2.50%; panthenol, 0.10-2.50%; mono-, di-, or tri-glyceryl caprylate, about 1%; L-valine, 0.025-0.65%; L-isoleucine, 0.0075-0.20%; L-leucine, 0.015-0.35%; glycerin, 0.50-15.0%; polyoxypropylene-2 myristyl ether propionate, 0.50-15.0%; glyceryl stearate/PEG 100 stearate, 1.00-20.0%; cetyl alcohol/stearyl alcohol, 1.00-20.0%; cyclomethicone, 0.25-7.50%; polydimethylsiloxane, 0.25-5.00%; stearic acid, 0.25-6.50%; evening primrose (*Oenothera Biennis*) oil, 0.05-1.25%; babassu (*Orbignya oleifera*) oil, 0.05-1.25%; avocado (*Persea aratissima*) oil, 0.05-1.25%; safflower (*Carthamus tinctorius*) oil, 0.05-1.25%; olive (*Olea europaea*) oil, 0.05-1.25%; 2-phenoxyethanol, 0.05-1.25%; sodium hydroxymethylglycinate, 0.10-2.50%; and disodium EDTA 0.01-0.25%.

16. The method of claim 1, wherein the composition consists essentially of deionized water QS %; biotin 0.050% wt.; vitamin E 0.500% wt.; serine 0.066% wt.; vitamin B6 0.500% wt.; panthenol 0.500% wt.; mono-, di-, or tri-glyceryl caprylate about 1.000%; valine 0.134% wt.; isoleucine 0.039% wt.; leucine 0.070% wt.; glycerin 3.000% wt.; PPG-2 Myristyl Ether Propionate 3.000% wt.; glyceryl stearate/PEG 100-Stearate 4.500% wt.; cetyl alcohol/stearyl alcohol 4.000% wt.; cyclomethicone 1.500% wt.; polydimethylsiloxane 1.000%; stearic acid 1.250% wt.; evening primrose (*Oenothera Biennis*) oil 0.250% wt.; babassu (*Orbignya Oleifera*) oil 0.250% wt.; avocado (*Persea Gratissima*) oil 0.250% wt.; safflower (*Carthamus Tinctorius*) oil 0.250% wt.; olive (*Olea Europaea*) oil 0.250% wt.; 2 Phenoxyethanol 0.250% wt.; sodium hydroxymethylglycinate 0.500% wt.; and disodium EDTA 0.050% wt.

17. The method of claim 1 wherein the persons age is between 16 and 46.

18. The method of claim 1, wherein the topical composition further comprises one or more of serine, glycine, alanine and threonine.

19. The method of claim 1, wherein the skin symptom due to a dermatological condition selected from the group consisting of: allergic contact dermatitis, irritant contact dermatitis, radiation dermatitis, seborrheic dermatitis, eczematous skin symptoms, diabetic skin symptoms, stasis skin symptoms, and sunburn skin symptoms.

20. The method of claim 1, wherein the dermatological condition is dermatitis and the skin symptom or skin symptoms develop from dermatitis.

21. The method as recited in claim 1 wherein improvement of the symptoms is seen after two weeks of topical administration.

22. The method of claim 1 wherein the reoccurrence of skin symptoms is suppressed for at least two weeks from when treatment stops.

23. The method of claim 1 wherein the topical composition further comprises 0.25% 2-Phenoxyethanol and 0.050% disodium EDTA as preservatives.

* * * * *